(12) United States Patent
Bruno

(10) Patent No.: US 9,772,263 B2
(45) Date of Patent: Sep. 26, 2017

(54) SAMPLING SYSTEM AND PROCESS FOR SAMPLING

(71) Applicant: NATIONAL INSTITUTE OF STANDARDS AND TECHNOLOGY, Gaithersburg, MD (US)

(72) Inventor: Thomas J. Bruno, Broomfield, CO (US)

(73) Assignee: THE UNITED STATES OF AMERICA, AS REPRESENTED BY THE SECRETARY OF COMMERCE, Washington, DC (US)

( * ) Notice: Subject to any disclaimer, the term of this patent is extended or adjusted under 35 U.S.C. 154(b) by 295 days.

(21) Appl. No.: 14/570,068

(22) Filed: Dec. 15, 2014

(65) Prior Publication Data
US 2015/0140673 A1 May 21, 2015

Related U.S. Application Data

(63) Continuation-in-part of application No. 13/974,181, filed on Aug. 13, 2013.

(60) Provisional application No. 61/692,777, filed on Aug. 24, 2012.

(51) Int. Cl.
G01N 1/22 (2006.01)
G01N 1/44 (2006.01)
G01N 1/40 (2006.01)
G01N 30/06 (2006.01)

(52) U.S. Cl.
CPC ......... *G01N 1/2226* (2013.01); *G01N 1/4022* (2013.01); *G01N 1/44* (2013.01); *G01N 2001/2229* (2013.01); *G01N 2030/062* (2013.01); *Y10T 436/142222* (2015.01); *Y10T 436/173076* (2015.01); *Y10T 436/212* (2015.01); *Y10T 436/218* (2015.01); *Y10T 436/25875* (2015.01)

(58) Field of Classification Search
CPC ........................... G01N 1/2226; G01N 1/4022
See application file for complete search history.

(56) References Cited

U.S. PATENT DOCUMENTS 6,074,461 A * 6/2000 Wilson .................. G01N 30/28
96/102

OTHER PUBLICATIONS

Simple Quantitative Headspace Analysis by Cryoadsorption on a Short Alumina PLOT Column Journal of Chromatographic Science vol. 47, Aug. 2009.*

(Continued)

*Primary Examiner* — Krishnan S Menon
*Assistant Examiner* — Dwan A Gerido
(74) *Attorney, Agent, or Firm* — Toby D. Hain

(57) ABSTRACT

A sampling system includes an analyte sampler that includes an enclosure; a mount disposed in the enclosure; a capillary tube disposed in the mount; and a thermal member disposed in the enclosure and including a first fluid supply member to provide a fluid to an interior of the enclosure. The sampling system also includes a manifold in fluid communication with the analyte sampler. A process for sampling an analyte includes subjecting the capillary tube to a negative pressure; and controlling the temperature of the capillary tube to immobilize the analyte in the capillary tube; providing an analyte to a second end of the capillary tube; and immobilizing the analyte in the capillary tube to sample the analyte.

16 Claims, 17 Drawing Sheets

(56) References Cited

OTHER PUBLICATIONS

Bruno, T.J. Simple, Quantitative Headspace Analysis by Cryoadsorption on a Short Alumina PLOT Column Journal of Chromatographic Science 2009, 47, 5069-5074.

Lovestead, T.M.; Bruno, T.J. Detection of poultry spoilage markers from headspace analysis with cryoadsorption on a short alumina PLOT column, Food Chemistry 2010, 121. 1274-1282.

Lovestead, T.M.; Bruno, T.J. Trace Headspace Sampling for Quantitative Analysis of Explosives with Cryoadsorption on Short Alumina Porous Layer Open Tubular Columns, Anal. Chem. 2010, 82,5621-5627.

Lovestead, T.M.; Bruno, T.J. Detecting gravesoil with headspace analysis with adsorption on short porous layer open tubular (PLOT) columns, Forensic Science International, 2011 204,156-161.

Nichols, J, et al Analysis of arson fire debris by low temperature dynamic headspace adsorption porous layer open tubular columns Journal of Chromatography A 2014 1334, 126-138.

Bruno, T.J.; Nichols, J., Method and apparatus for pyrolysis—Porous layer open tubular column—Cryoadsorption headspace sampling and analysis, Journal of Chromatography A 2013 1286, 192-199.

* cited by examiner

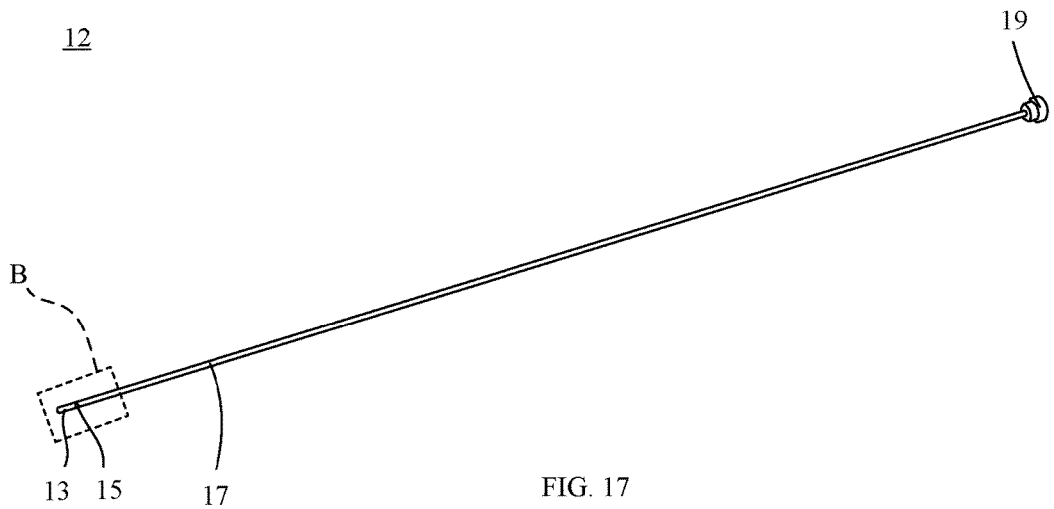
FIG. 17
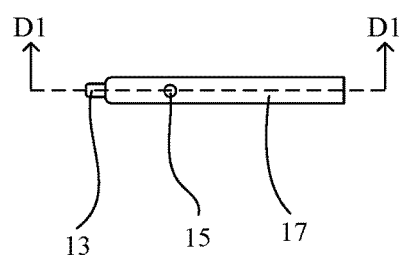
FIG. 18
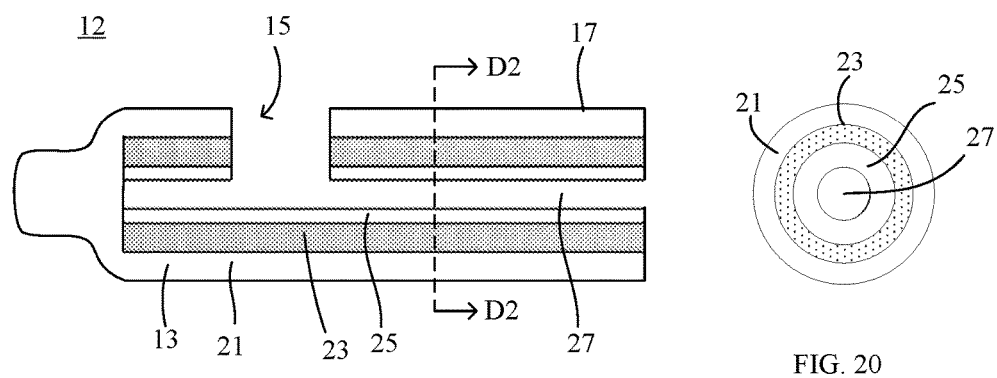
FIG. 19
FIG. 20

SAMPLING SYSTEM AND PROCESS FOR SAMPLING

CROSS REFERENCE TO RELATED APPLICATIONS

The present invention is a continuation-in-part of U.S. patent application Ser. No. 13/974,181 filed Aug. 23, 2013, the disclosure of which is incorporated herein by reference in its entirety, and which claims the benefit of U.S. Provisional Patent Application Ser. No. 61/692,777 filed Aug. 24, 2012, the disclosure of which is incorporated herein by reference in its entirety.

STATEMENT REGARDING FEDERALLY SPONSORED RESEARCH

This invention was made with United States government support from the National Institute of Standards and Technology. The government has certain rights in the invention.

BACKGROUND

Headspace sampling devices and systems typically include a vial configured to receive and hold a sample and to receive a sparging or inert gas. The gas carries headspace vapor from the vial to an analytical device. The vial may include a diaphragm or septum to seal the vial such that a probe can be inserted in the septum to provide a flow of the sparging gas from the sample headspace in the vial for transmission of the gas to an analytical instrument, which analyzes the headspace gas.

Sampling methods from headspaces may be either static or dynamic. In static methods, one typically pressurizes a sealed vial or vessel containing the condensed analyte (to slightly above atmospheric pressure), then sampling may be done of the pressurized headspace through a septum. Sampling may be done with a gas tight syringe (with or without a syringe valve), a multiport sampling valve, or with a solid phase micro extraction (SPME) fiber. In dynamic methods, a flow of carrier or sweep gas may be applied to the matrix containing the analyte. The stream may then be collected in a cryostat, adsorbent or solvent, thus this method is often referred to as purge and trap. The sweep gas may be under a positive pressure or drawn through the sample at reduced pressure.

When the analyte in the headspace gas is at a trace level, or when an exhaustive analysis of all constituents is desired, purge and trap methods are often preferred over static headspace or even modern SPME approaches. For analytes of very low volatility, longer collection times are required to collect sufficient sample for analysis. One means of obtaining a sample and introducing it into an analytical instrument, such as a chromatographic column, is known as headspace sampling. In conventional headspace sampling, sample material is sealed in a vial and subjected to constant temperature conditions for a specified time. Analyte concentrations in the vial gas phase should reach equilibrium with the liquid and/or solid phases during this thermostatting time. The vial is subsequently pressurized with carrier gas to a level greater than the "natural" internal pressure resulting from thermostatting and equilibration. Then the pressurized vial is connected to the chromatographic column in such a way as to allow for the transfer of a portion of the vial gas phase into the column for a short period of time.

Gas chromatography is an analytical instrument used for the separation of compounds for the purpose of purification, identification, and quantification. The sparging gas having the sample entrained therein can be injected into a gas chromatograph for compositional analysis and to provide an output that indicates a substance in the sample.

The art is receptive to articles and processes that provide for sampling an analyte.

BRIEF DESCRIPTION

The above and other deficiencies are overcome by, in an embodiment, a sampling system comprising: an analyte sampler comprising: an enclosure; a mount disposed in the enclosure; a capillary tube disposed in the mount and configured to receive an analyte; and a thermal member disposed in the enclosure and configured to pneumatically control a temperature of the capillary tube, the thermal member comprising a first fluid supply member to provide a fluid to an interior of the enclosure; and a manifold in fluid communication with the analyte sampler.

Further disclosed is a process for sampling an analyte, the process comprising: subjecting a capillary tube disposed in an analyte sampler to a negative pressure, the analyte sampler comprising: an enclosure; a mount disposed in the enclosure; the capillary tube disposed in the mount and configured to receive the analyte; and a thermal member disposed in the enclosure and configured to pneumatically control a temperature of the capillary tube, the thermal member comprising a first fluid supply member to provide a fluid to an interior of the enclosure; and controlling the temperature of the capillary tube, wherein the temperature is effective to immobilize the analyte in the capillary tube; providing an analyte to a second end of the capillary tube; and immobilizing the analyte in the capillary tube to sample the analyte.

BRIEF DESCRIPTION OF THE DRAWINGS

The following descriptions should not be considered limiting in any way. With reference to the accompanying drawings, like elements are numbered alike:

FIG. 17 shows a photograph of a probe;
FIG. 18 shows an enlarged view of a probe tip of the probe shown in FIG. 17;
FIG. 19 shows a cross-section along line D1-D1 of the probe shown in FIG. 18;

FIG. 20 shows a cross-section along line D2-D2 of the probe shown in FIG. 19;

DETAILED DESCRIPTION

Figure 1:
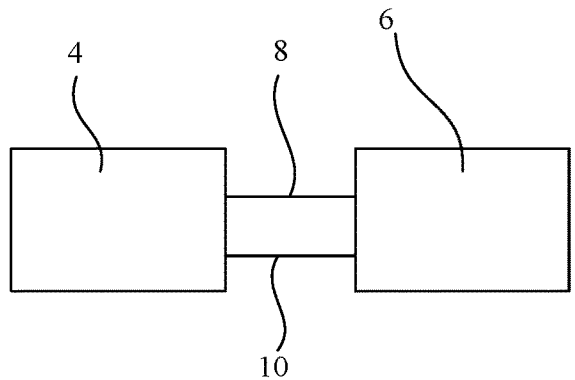
FIG. 1 shows an embodiment of a sampling system.

A detailed description of one or more embodiments is presented herein by way of exemplification and not limitation.

It has been discovered that a sampling system herein is configured as a portable article for use in an environment outside a laboratory. Advantageously, the analyte sampler is useful in applications in criminalistics, food safety, and the environment. According to an embodiment, the sampling system includes an analyte sampler, manifold, flow member to interconnect the analyte sampler and manifold, and an optional probe to acquire and analyte from a sample. The analyte sampler is configured to be remotely operable and robust. The manifold is configured to be portable and robust. The flow member is configured to be flexible, portable, and efficient. Additionally, the probe is configured to acquire the analyte from a simple that includes, e.g., a soil, tank, freight container, motor vehicle, and the like. Further, it is contemplated that the analyte sampler includes a capillary tube and is configured to be subjected to a selected temperature such that the analyte is disposed in the capillary tube by subjecting the capillary tube to the negative pressure instead of a positive pressure approach.

According to an embodiment, a sampling system includes an analyte sampler that includes an enclosure; a mount disposed in the enclosure; a capillary tube disposed in the mount and configured to receive an analyte; and a thermal member disposed in the enclosure and configured to pneumatically control a temperature of the capillary tube, the thermal member comprising a first fluid supply member to provide a fluid to an interior of the enclosure. The sampling system also includes a manifold in fluid communication with the analyte sampler. The sampling system further includes a flow member to interconnect the manifold and the analyte sampler. The flow member includes a second fluid supply member to communicate the fluid from the manifold to the first fluid supply member and a fluid return to communicate the fluid from the enclosure to the manifold. The sampling system additionally includes a vacuum member to generate a negative pressure and a vacuum line to connect the vacuum member to a first end of the capillary tube and to subject an interior of the capillary tube to the negative pressure. The sampling system also includes a probe connected to a second end of the capillary tube, a temperature controller to selectively control a temperature of the thermal member, or a combination thereof. The temperature controller includes a first temperature control member to produce a cold fluid from the fluid and a second temperature control member to produce a hot fluid from fluid, wherein the fluid provided to the interior of the enclosure includes the cold fluid or the hot fluid. Additionally, the manifold includes the vacuum member, the first temperature control member, and the second temperature control member.

In an embodiment, the enclosure is a hand piece or sampling module. In certain embodiments, the vacuum member, the first temperature control member, the second temperature control member, and the flow member independently are configured to connect to a fluid source, a fluid dump, or a combination thereof. According to an embodiment, the enclosure is configured to receive the fluid from the second fluid supply member and to recycle the fluid to the fluid return. The capillary tube can include a porous layer open tubular column. The probe can include a body, a probe tip disposed at an end of the body, and a sampling orifice disposed proximate to the probe tip. In an embodiment, the flow member includes a thermal insulation surroundingly disposed on the second fluid supply member or the fluid return and a spacer interposed between the second fluid supply member and the thermal insulation. In an embodiment, the flow member is configured such that a direction of flow of the fluid in the second fluid supply member is counter to a direction of flow of the fluid in the fluid return. In a certain embodiment, the second fluid supply member and the fluid return are coaxially disposed in the flow member. In some embodiments, the second fluid supply member and the fluid return are adjacently disposed in the flow member.

According to an embodiment, as shown in FIG. 1, sampling system 2 includes analyte sampler 4 connected to manifold 6 via flow member 8 and vacuum line 10. Analyte sampler 4 is configured to sample a sample and to receive an analyte from the sample. Manifold 6 is configured to subject analyte sampler 4 to a selected temperature or a negative pressure. The analyte is disposed to be stored in analyte sampler 4 in response to application of the negative pressure and a selected temperature effective to immobilize the analyte therein.

Figure 2:
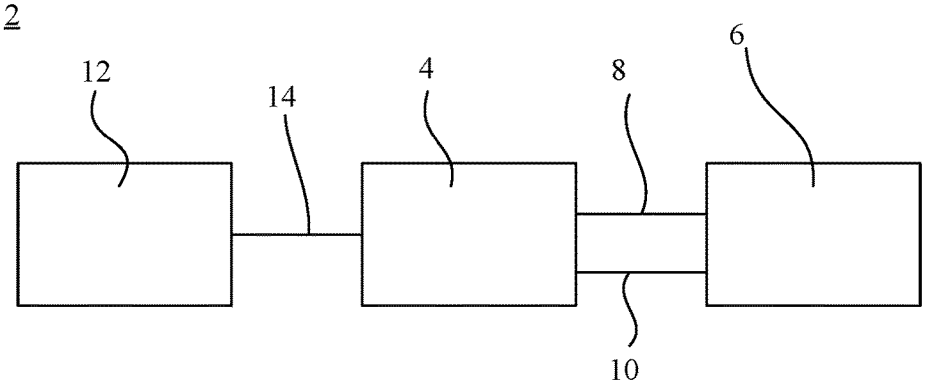
FIG. 2 shows an embodiment of a sampling system.

In some embodiments, sampling system 2 includes probe 12 connected to analyte sampler 4 via probe line 14 as shown in FIG. 2. Probe 12 is configured to receive the analyte and to communicate the analyte through probe line 14 to analyte sampler 4.

Figure 3:
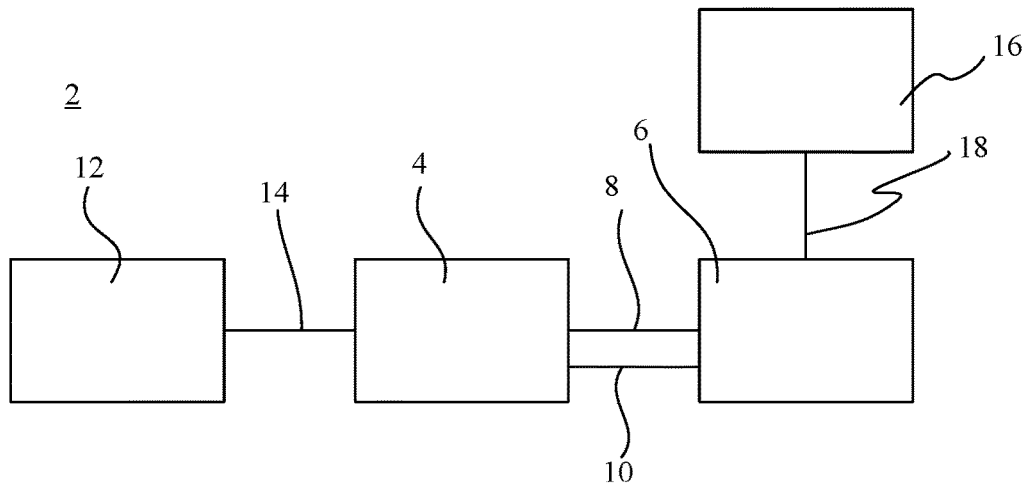
FIG. 3 shows an embodiment of a sampling system.

With reference to FIG. 3, in an embodiment, sampling system 2 includes fluid source 16 connected to manifold 6 via fluid line 18. Fluid line 18 interconnects and communicates fluid from fluid source 16 manifold 6. Manifold 6 is configured to receive the fluid from fluid source 16 and to communicate the fluid to analyte sampler 4 through flow member 8. In some embodiments, manifold 6 is configured to change a temperature of the fluid has received from fluid source 16 by increasing the temperature of fluid to produce a hot fluid, decreasing the temperature of the fluid to produce a cold fluid, or combination thereof. In addition, manifold 6 is configured to produce a negative pressure using the fluid.

Figure 4:
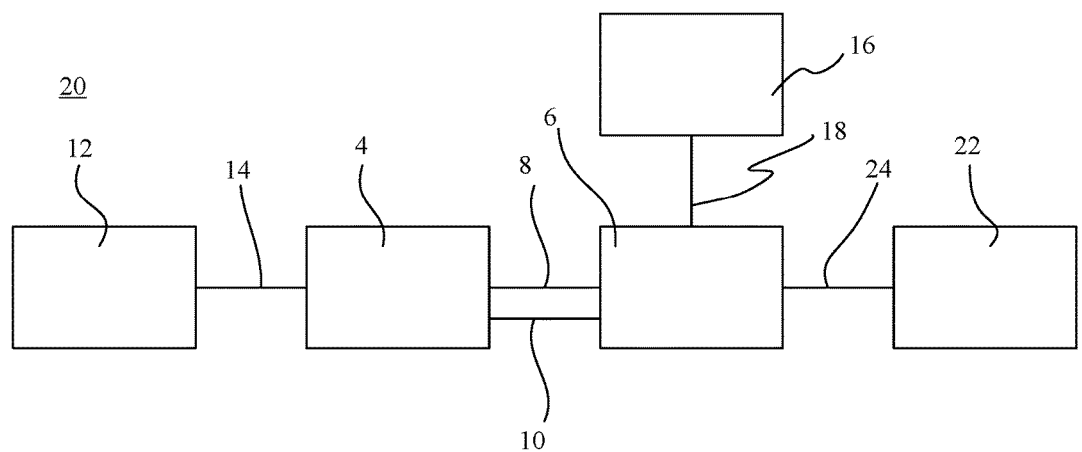
FIG. 4 shows an embodiment of an analyzer.

According to an embodiment, as shown in FIG. 4, analyzer 20 includes sampling system 2 and detector 22 interconnected by transfer line 24. The analyte received by analyte sampler 4 is communicated to detector 22 through manifold 6 (e.g., through a by-pass line (not shown) disposed in manifold 6 to communicate the analyte from analyte sampler 4 to transfer line 24) and transfer line 24. Detector 22 is configured to receive the analyte and to perform analysis on the analyte. Exemplary analyses include separation, ionization, mass spectrometry, chromatography, pyrolysis and the like to detect the analyte, an adduct of the analyte with another chemical species, a reaction product of the analyte, a dissociation product of the analyte, an electrically charged (positive, negative, or zwitterionic) or neutral form of the analyte, emission (e.g., fluorescence, chemiluminescence, phosphorescence, and the like) from the analyte, light scattering by the analyte, transmission of light through the analyte, absorption of light by the analyte, circular dichroism, or a combination thereof.

According to an embodiment, analyzer 20 includes sampling system 2 connected by transfer line 24 to an auxiliary member (not shown). The analyte received by analyte sampler 4 is communicated to the auxiliary member through manifold 6 (e.g., through a by-pass line (not shown) disposed in manifold 6 to communicate the analyte from analyte sampler 4 to transfer line 24) and transfer line 24. Alternatively, the auxiliary member can be connected directly to analyte sampler 4 for collection of the analyte. The auxiliary member can be a storage container to receive the analyte, a sorption trap (that includes, e.g., a zeolite or the like, and the like. The auxiliary member is configured to receive or store the analyte for later analysis or to delay analysis of the analyte. In some embodiments, the auxiliary member includes a reagent to react with the analyte, e.g., to form a stable product for storage or later analysis or to provide a qualitative or initial identification test as to the identity of the analyte.

Figure 5:
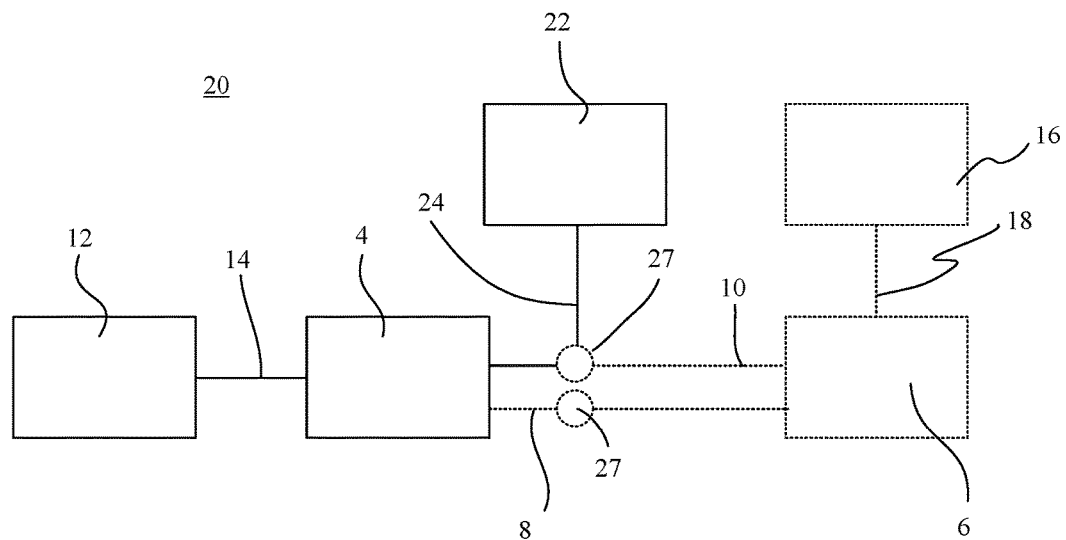
FIG. 5 shows an embodiment of an analyzer.

In an embodiment, as shown in FIG. 5, analyzer 20 includes detector 22 connected to analyte sampler 4 and is configured to receive the analyte from analyte sampler 4 via communication of the analyte through transfer line 24. Valve 27 is optionally interposed between analyte sampler 4 and detector 22. Manifold 6 is optionally connected to valve 27. In this configuration, valve 27 (when present) selectively interconnects analyte sampler 4 to detector 22, manifold 6, or a combination thereof. In this manner, analyte sampler 4 can be isolated from detector 22 (due to valve 27) while a negative pressure is subjected to analyte sampler 4 from manifold 6 via vacuum line 10 to acquire the analyte and immobilize the analyte in analyte sampler 4 such that thereafter transfer line 10 from manifold 6 is isolated from analyte sampler 4 by valve 27, which valve 27 then either connects analyte sampler 4 to detector 22 (to communicate the analyte to detector 22 via transfer line 24) or isolates analyte sampler 4 from detector 22 (to block communication of the analyte to detector 22 via transfer line 24). In some embodiments, valve 27 isolates analyte sampler 4 from both detector 22 and manifold 6 (vacuum line 10, flow member, or combination thereof), isolates analyte sampler 4 from one of detector 22 or manifold six, or connects both detector 22 and manifold 6 analyte sampler 4.

Figure 6:
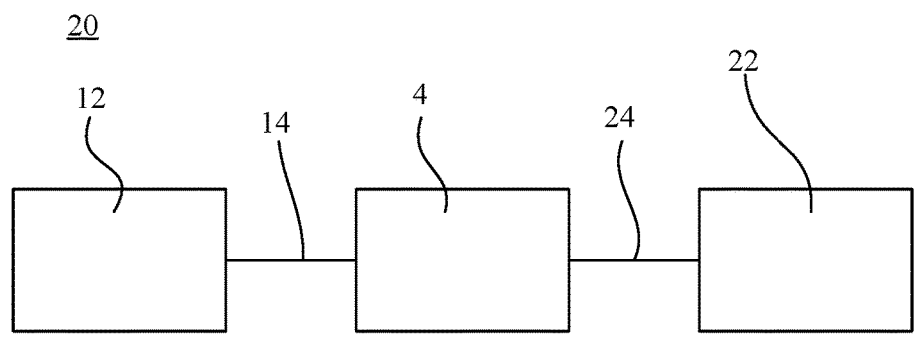
FIG. 6 shows an embodiment of an analyzer.

According to an embodiment, with reference to FIG. 6, analyzer 20 includes probe 12 connected to analyte sampler 4 via probe line 14 and detector 22 connected to analyte sampler 4 via transfer line 24. Here, probe 12 is configured to sample the sample and to receive the analyte whereafter the analyte is communicate through probe line 14 to analyte sampler 4. Probe 12 or probe line 14 can be subjected to the negative pressure from manifold 6.

Figure 7:
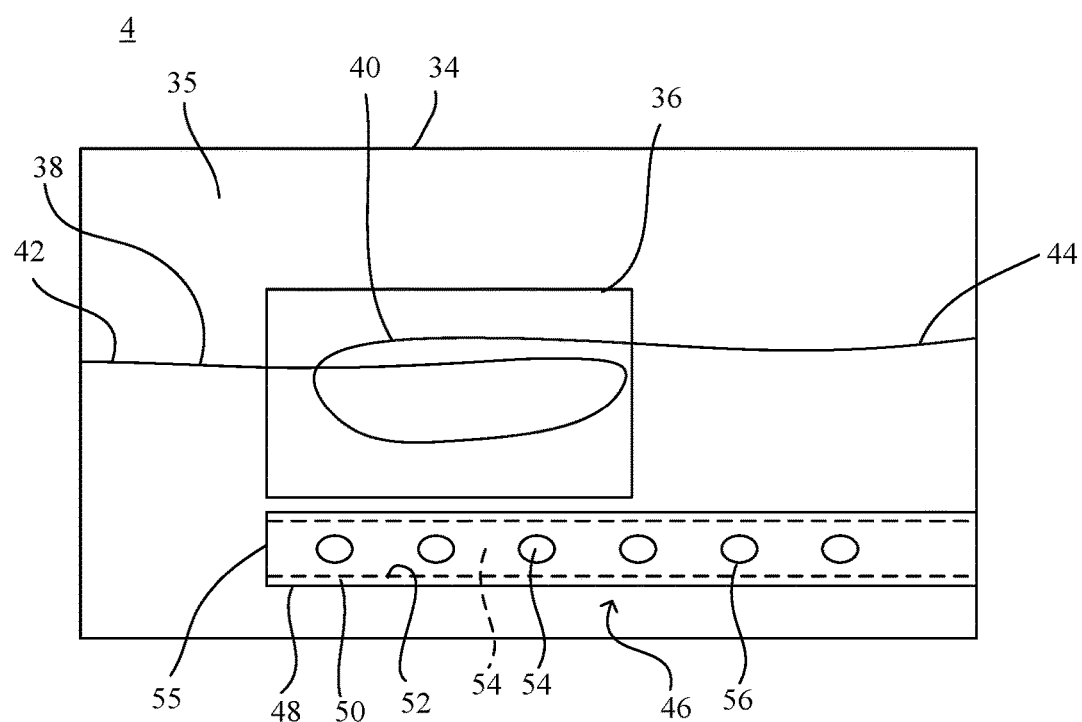
FIG. 7 shows a top view of an analyte sampler.

Analyte sampler 4 is configured to receive the analyte. A top view of an embodiment of analyte sampler 4 (with a lid of analyte sampler 4 removed) is shown in FIG. 7. Here, analyte sampler 4 includes enclosure 34 having interior 35 to contain mount 36 disposed therein. Capillary tube 38 includes embedded portion 40 that is disposed in mount 36, first end 44, and second end 42. First end 42 and second 44 are in fluid communication with an external environment outside of enclosure 34. That is, first end 42 receives the analyte from a source external to enclosure 34. The analyte is communicated through embedded portion 40 (which can include a residence time in which the analyte is immobilized in capillary tube 38) to second end 44 and further communicated from second end 44 to a position external to enclosure 34, e.g., to detector 22 or manifold 6. Additionally, thermal member 46 is disposed in interior 35 of enclosure 34. Thermal member 46 can be, e.g., a tubular that includes outer wall 50 and a hollow interior such as first fluid supply member 48 to communicate a fluid from fluid source 16 or manifold 6. The fluid flows through first fluid supply member 48 along fluid path 54 that is bounded by inner surface 52 of outer wall 50. The fluid exits from the first fluid supply member 48 is communicated through orifice 56 and to interior 35 of enclosure 34. The fluid provided by thermal member 46 controls a temperature of capillary tube 38 or interior 35 such that capillary tube 38 to be subjected selected temperature. Further, the temperature of capillary tube 38 subjected to the fluid from thermal member 46 can be changed by changing the temperature of the fluid. In an embodiment, the cold fluid provided from thermal member 46 cools capillary tube 38 to a first temperature to immobilize the analyte in capillary tube 38, e.g., to store the analyte therein or to increase a residence time in capillary tube 38. According to an embodiment, the fluid provided from thermal member 46 heats capillary tube 38 to a second temperature to mobilize the analyte disposed in capillary tube 38, e.g., to communicate the analyte from capillary tube 38 to manifold 6 or detector 22. With respect to the top view of analyte sampler 4 shown in FIG. 7, thermal member 46 is shown disposed laterally proximate to mount 36. In some embodiments, the thermal member 46 is disposed beneath mount 36 and capillary tube 38 (i.e., behind the plane of the drawing for FIG. 7, e.g., as shown in an embodiment of analyte sampler 4 shown in FIG. 16).

In an embodiment, a plurality of thermal members 46 or disposed in enclosure 34 to pneumatically control a temperature of capillary member 38. As used herein, "pneumatically" (as well as other forms of the word "pneumatic") refers to controlling (e.g., maintaining or changing) a temperature of capillary member 38 by providing a fluid to interior 35. Without wishing to be bound by theory, it is believed that thermal transfer between capillary tube 38, mount 36, and the fluid controls the temperature of capillary tube 38. For controlling the temperature of capillary tube 38 at a constant temperature, the fluid is provided at a selected temperature to equilibrate the temperature of capillary tube 38. For controlling the temperature of capillary tube 38 to higher temperature or lower temperature, the fluid is provided to interior 35 respectively at a temperature greater than or less than the temperature of capillary tube 38.

The fluid provided to interior 35 from thermal member 46 is communicated through orifice 56 from first fluid supply member 48. FIG. 7 shows a plurality of orifices 56 disposed along a length of first fluid supply member 48. A shape of orifice 56 can be any shape (e.g., circular, polygonal, elliptical, and the like) effective to communicate the fluid. A spacing between adjacent orifices 56 can be selected. According to an embodiment, orifice 56 is an open aperture absent any material disposed therein. In some embodiments, a material is disposed in orifice 56 to filter or disperse the fluid from fluid flow path 54 into interior 35 of enclosure 34. A position of orifices 56 is not limited to being distributed along the wall 52 of thermal member 46. In an embodiment, orifice 56 is disposed at end 55 of first fluid supply member 48.

A distance between thermal member 46 and mount 36 or capillary tube 38 can be selected to be effective for thermal transfer of energy between capillary tube 38 and the fluid provided by thermal member 46 to control the temperature of capillary tube 38. A shape of thermal member 46 can be any shape effective to attain a selected temperature of capillary tube 38. Exemplary shapes of thermal member 46 include linear as shown in FIG. 7, curved, serpentine, circular, and the like.

Thermal member 46 can include any material effective to deliver the fluid, provide heat transfer between the fluid in first fluid supply member 48 and interior 35, thermally insulate fluid in first fluid supply member 48 and interior 35, or the like. Exemplary materials for thermal member 46, particularly for wall 50, include a plastic (e.g., polytetrafluoroethylene (PTFE), polyvinyl chloride, and the like), metal (e.g., copper, stainless steel, and the like), glass, ceramic, and the like.

Enclosure 34 in which capillary tube 38, mount 36, and thermal member 46 are disposed can be any shape to contain these elements. Enclosure 34 can be pliable or rigid; thermally insulating or thermally conductive; selectively transmissive, reflective, or absorptive to a wavelength of radiation (e.g., ultraviolet, visible, near infrared, infrared, and the like), and the like. According to an embodiment, enclosure 34 includes PTFE.

Capillary tube 38 disposed in mount 36 includes an outer wall and a flow path disposed therein for communicating or immobilizing the analyte. In an embodiment, capillary tube 38 is a porous layer open tubular (PLOT) capillary tube. Exemplary capillary tubes are described in U.S. patent application Ser. No. 13/974,181 filed Aug. 23, 2013, and U.S. Provisional patent application Ser. No. 61/692,777 filed Aug. 24, 2012, the disclosure of each of which is incorporated by reference herein in their entirety.

Mount 36 rigidly constrains capillary tube 38 so that embedded portion 40 is not free to move or bend. Additionally, mount 36 includes a material that provides thermal transfer between embedded portion 40 of capillary tube 38 and the fluid provided from thermal member 46. Capillary tube 38 can be completely or partially disposed in mount 36. In an embodiment, capillary tube 38 is completely disposed in mount 36 such that first end 42 and second end 44 are disposed in mount 36. Here, additional to tubulation (not shown) can be disposed in interior 35 to connect capillary tube 38 to external elements outside of enclosure 34 (see, e.g., transfer line 122 shown in FIG. 16).

Mount 36 can be in direct contact with enclosure 34 or can indirectly contact enclosure 34. In an embodiment, mount 36 is stood off from enclosure 34 with a spacer such that mount 36 indirectly contacts enclosure 34. The spacer can be thermally conductive or thermally isolating. Exemplary materials for mount 36 include a metal, plastic, and the like. The plastic can be a thermoset polymer or a thermoplastic polymer. A thermoset polymer solidifies when first heated under pressure, and thereafter may not melt or mold without destroying the original characteristics. Suitable thermosetting polymeric materials may include one or more epoxides, phenolics, melamines, ureas, polyurethanes, polysiloxanes, or polymers including a suitable crosslinkable functional moiety. According to an embodiment, mount 36 includes polyurethane.

A thermoplastic polymer has a macromolecular structure that repeatedly softens when heated and hardens when cooled. Illustrative examples of thermoplastic polymeric materials include an olefin-derived polymer, e.g., polyethylene, polypropylene, and their copolymers; polymethylpentane-derived polymers, e.g., polybutadiene, polyisoprene, and their copolymers; polymers of unsaturated carboxylic acids and their functional derivatives, e.g., acrylic polymers such as poly (alkyl acrylates), poly (alkyl methacrylate), polyacrylamides, polyacrylonitrile, and polyacrylic acid; alkenylaromatic polymers, e.g., polystyrene, poly-alpha-methylstyrene, polyvinyltoluene, and rubber-modified polystyrenes; polyamides, e.g., nylon-6, nylon-66, nylon-11, and nylon-12; polyesters, such as, poly(alkylene dicarboxylates), especially poly(ethylene terephthalate) (PET), poly (1,4-butylene terephthalate) (PBT), poly(trimethylene terephthalate) (PTT), poly(ethylene naphthalate) (PEN), poly(butylene naphthalate) (PBN), poly(cyclohexanedimethanol terephthalate), poly(cyclohexanedimethanol-co-ethylene terephthalate) (PETG), and poly(1,4-cyclohexanedimethyl-1,4-cyclohexanedicarboxylate) (PCCD), and poly (alkylene arenedioates); polycarbonates; co-polycarbonates; co-polyestercarbonates; polysulfones; polyimides; polyarylene sulfides; polysulfide sulfones; and polyethers such as polyarylene ethers, polyphenylene ethers, polyethersulfones, polyetherimides, polyetherketones, polyetheretherketones; or blends or copolymers thereof.

Figure 8:
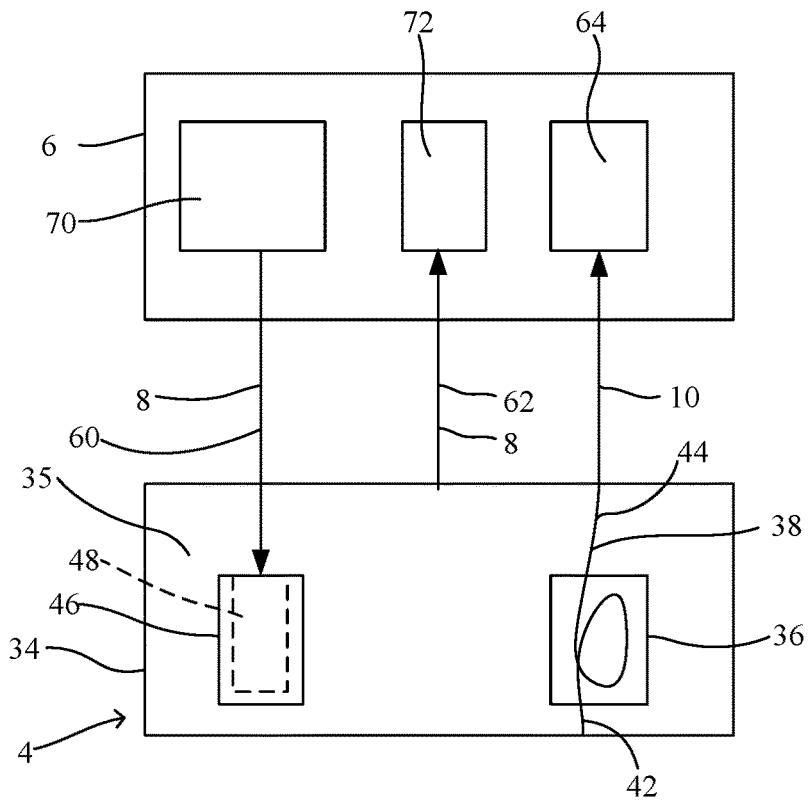
FIG. 8 shows a top view of a sampling system.

According to an embodiment, analyte sampler 4 is in flow communication with manifold 6 as shown in FIG. 8. Here, manifold six includes temperature controller 70, fluid dump 72, and vacuum member 64. Temperature controller 70 provides fluid at a selected temperature to thermal member 46 that includes second fluid supply member 60. The fluid exits thermal member 46, interacts with capillary tube 38 and mount 36 via heat transfer, and exits enclosure 34 through flow member 8. That is, the fluid is communicated from enclosure 34 to fluid dump 72 through fluid return 62 disposed in the flow member 8. Additionally, the vacuum member 64 produces the negative pressure that is communicated through vacuum line 10 to capillary tube 38. In this manner, the analyte is received by capillary tube 38 at a first end 42, and the direction of movement of the analyte through capillary tube 38 proceeds from first end 42 to second end 44. It is contemplated that various valves to isolate or shunt a flow of the fluid or the analyte can be disposed in the flow member 8 or vacuum line 10. Accordingly, in an embodiment, the analyte can be communicated from first end 42 to second end 44 as capillary tube 38 is subjected to the negative pressure from vacuum member 64. The analyte can be immobilized in capillary tube 38 at a selected temperature (e.g., a cryogenic temperature or a temperature effective to immobilize the analyte), and a valve (connecting capillary tube 38 to vacuum member 64) closed to isolate vacuum line 10 and vacuum member 64 from capillary tube 38 such that the analyte is not removed from capillary tube 38. Thereafter, in some embodiments, capillary tube 38 can be heated to mobilize the analyte in capillary tube 38, and the valve can be opened to communicate the analyte to manifold 6. In a particular embodiment, capillary tube 38 can be heated to mobilize the analyte in capillary tube 38, and the valve can be opened to communicate the analyte to detector 22 connected thereto (see, e.g., FIG. 5 or 6).

Figure 9:
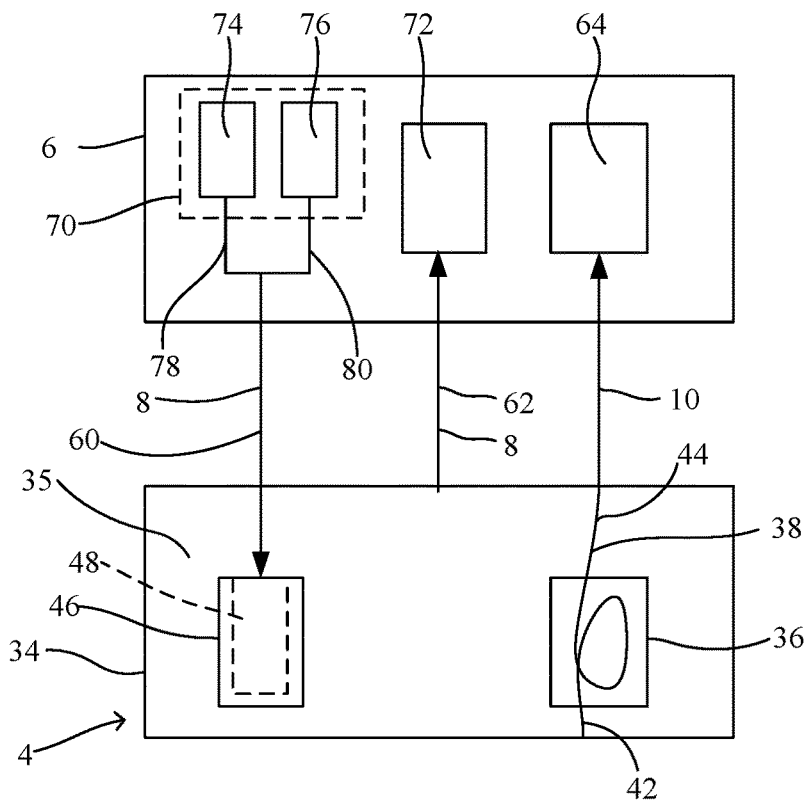
FIG. 9 shows a top view of a sampling system.

In an embodiment, as shown in FIG. 9, temperature controller 70 includes first vortex tube 74 and second vortex tube 76 that are configured to receive the fluid and respectively to produce a cold fluid (e.g., by cooling the fluid) or the hot fluid (e.g., by heating the fluid). First fluid line 78 is interposed between and interconnects first vortex tube 74 and flow member 8 to communicate the cold fluid from the first vortex tube 74 to second fluid supply member 60. Second fluid line 80 is interposed between and interconnects second vortex tube 76 and flow member 8 to communicate the hot fluid from the second vortex tube 76 to second fluid supply member 60.

Figure 10:
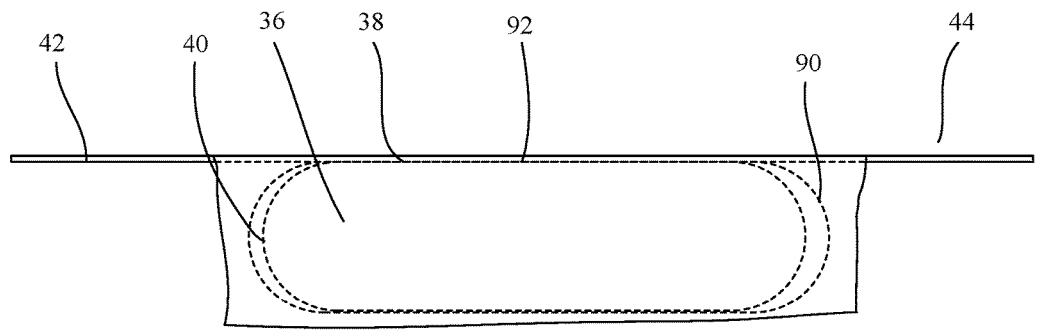
FIG. 10 shows a photograph of a capillary tube disposed in a mount.

An embodiment of capillary tube 38 disposed in mount 36 is shown in the photograph that is shown in FIG. 10. Here, capillary tube 38 is coiled and disposed in mount 36 (which is a molded epoxy wafer) such that embedded portion 40 includes a plurality of coils 90. Also, immobilizer 92 is disposed around and length of a portion of coils 90 to hold them together as mount 36 is formed around embedded portion 40. First end 42 protrudes from mount 36 to connect capillary tube 38, e.g., to a probe to receive the analyte. Second end 44 protrudes from mount 36 to connect capillary tube 38, e.g., to detector 22, vacuum line 10, manifold 6, vacuum member 64, and the like.

Figure 11:
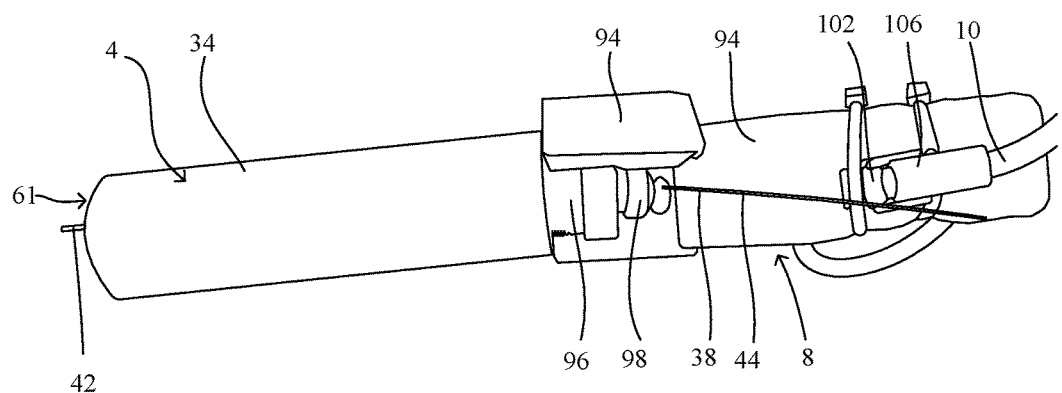
FIG. 11 shows a portion of a sampling system that includes an analyte sampler connected to a flow member.
Figure 12:
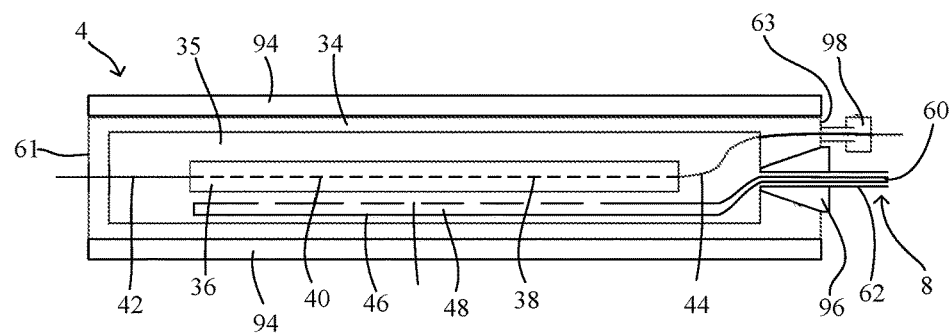
FIG. 12 shows a cross-section of an analyte probe.
Figure 13:
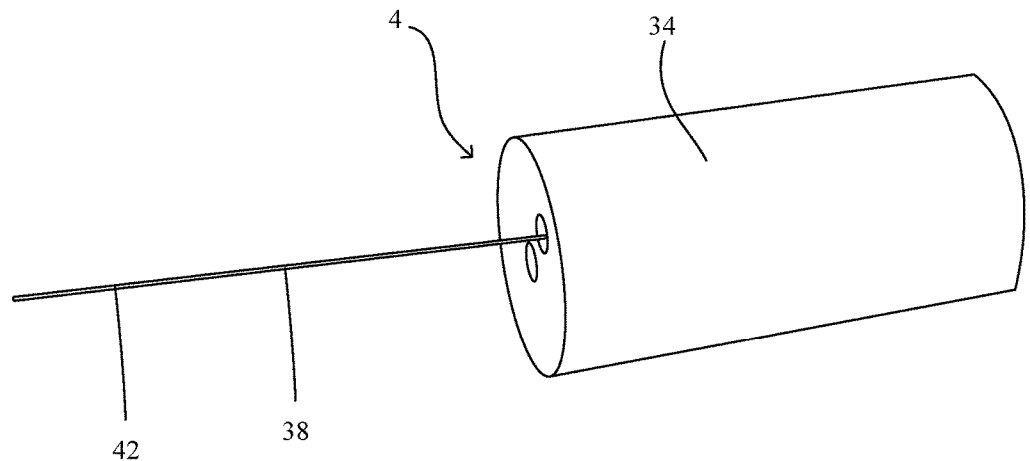
FIG. 13 shows a photograph of an end of the analyte sampler shown in FIG. 11.

Capillary tube 38, disposed in mount 36, is disposed in analyte sampler 4 for which an embodiment is shown in FIG. 11 (photograph), FIG. 12 (longitudinal cross-section), and FIG. 13 (end view of enclosure 34 and first end 42). Here, analyte sampler 4 is a hand piece. As used herein, "hand piece" refers to a member that can be disposed (e.g., held) and a hand, vise, clamp, mount, and the like such that the member may be removed or maintained stationary as capillary tube 38 receives the analyte. Thus, hand piece 34 allows analyte sampler 4 to easily be incorporated in a remote sampling system that is portable, wherein analyte sampler 4 been used as a wand to pass capillary tube 38 (or a probe attached thereto) over a sample or to insert capillary tube 38 (or probe attached to first end 44) into a sample to sample (e.g., receive or extract) the analyte from the sample. Accordingly, first end 42 protrudes from end 61 of enclosure 34, and capillary tube 38 extends from first and 42 through the amount 36 two second end 44 and second adapter 98, which is disposed at end 63 of enclosure 34. Installation 94 can be disposed along an exterior of enclosure 34, e.g., from end 61 to end 63 or can be disposed externally along flow member 8, which is connected to first adapter 96 at and 63 of enclosure 34. Here, flow member 8 includes second fluid supply member 62 supply the fluid from manifold 62 thermal member 46. The flow member 8 also includes fluid return 62 that receives the fluid provided to interior 35 from thermal member 46. In this arrangement, flow member 8 thus provides the fluid from manifold 6 to analyte sampler 34 through fluid communication along second fluid supply member 60 and receives the fluid from analyte sampler 34 to return the fluid to manifold 6 through fluid communication along fluid return 62. Installation 94 provides thermal insulation to the fluid disposed in and communicated by flow member 8 as well as provides thermal insulation to analyte sampler 4.

Figure 14:
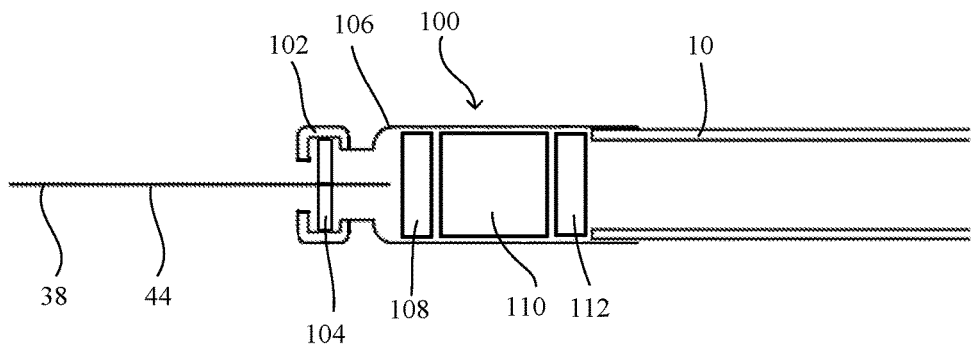
FIG. 14 shows a cross-section of a capillary tube disposed connected to a vacuum line.
Figure 15:
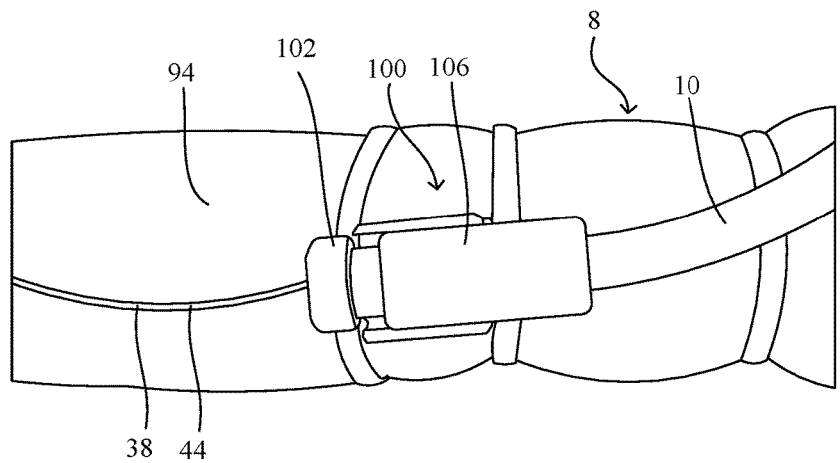
FIG. 15 shows a photograph of the capillary tube connected to the vacuum line for the sampling system shown in FIG. 11.

With reference to FIG. 11 (photograph), FIG. 14 (longitudinal cross-sectional view), and FIG. 15 (photograph), second end 44 of capillary tube 38 is in flow communication with manifold 6, detector 22, or combination thereof by interconnection, e.g., of vacuum line 10. In an embodiment, vacuum adapter 100 interfaces capillary tube 38 to vacuum line 10. Vacuum adapter 100 includes cap 102, seal 104 (e.g., a septum), and body 106. Seal 104 provides a seal between cap 102 and body 106, and vacuum line 10 is connected to body 106, e.g., by being adhered (e.g., bonded, glued, and the like), or press fit into body 106. Second end 44 of capillary tube 38 is inserted through seal 104. Adapter 104 optionally includes a filter that includes, e.g., first filter 108 (e.g., activated charcoal and the like), second filter 110, third filter 112, and the like. In an embodiment, vacuum adapter 100 is a septum vial that provides incorporation of an activated carbon filter to minimize a potential of sample vapors (e.g., the analyte) from entering manifold 6. This septum vial can be disposable, can have a long operation lifetime, and can be reusable.

Figure 16:
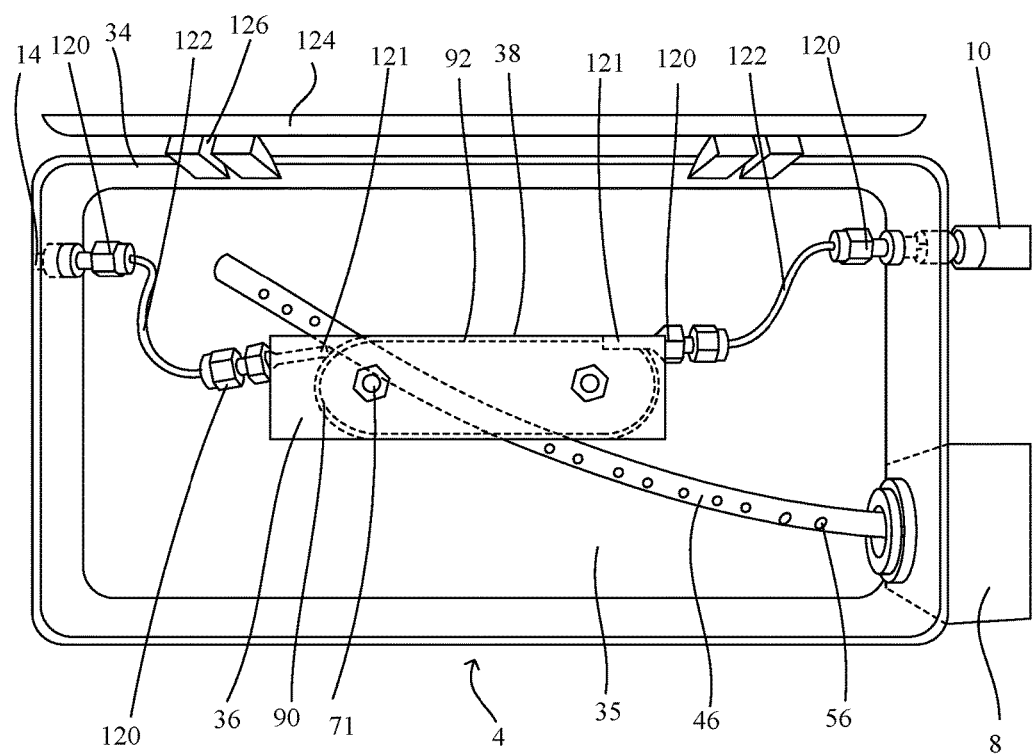
FIG. 16 shows a photograph of an analyte sampler.

According to an embodiment, as shown in the photograph shown in FIG. 16, analyte sampler 4 is a portable, remotely operable, and robust module. Here, capillary tube 38 is disposed in enclosure 34, which is a thermally insulating container, e.g. a hinged box made of a thermoplastic that can be covered with a thermally insulating material. Lid 124 can be removably disposed on enclosure with hinge 126. Here, capillary tube 38 includes embedded portion 40 that is disposed in mount 36. Mount 36 is disposed in enclosure 34 and separated from an interior wall of enclosure 34 with a standoff (not shown). The standoff can be a thermally insulating ceramic standoff through which fastener 71 is disposed to attach mount 36 to enclosure 34. Fasteners 71 can be, e.g., a screw, nut, pin, dowel, tube, and the like and may include thermally insulating materials, e.g., a metal such as series stainless steel, to minimize thermal conductivity between mount 36 and enclosure 34.

Probe line 14 (refer to, e.g., FIG. 2) Is connected to transfer adapter 120 that is connected to transfer line 122, which is in turn connected to adapter 121 that interfaces with capillary tube 38. Transfer adapters 120, 121 are, e.g., a tubing connector such as compression fittings that include O-rings, ferrules, nuts, unions, bulkhead connectors, tees, and the like. In this manner, probe 12 receives the analyte is communicated through probe line 14 to capillary tube 38 via transfer line 122. The analyte is then communicated from capillary tube 38 to vacuum line 10 via transfer line 122. Transfer line 122 can be a rigid or flexible tube that is a material compatible with the analyte, e.g., a metal or plastic tube.

According to an embodiment and shown in FIG. 16, adapter 121 is a 316 stainless steel compression fitting compatible with $\frac{1}{16}$-inch ($\frac{1}{16}$") diameter tube size. Adapters 121 disposed in mount 36 are connected to $\frac{1}{16}$" bulkhead fittings with interposed PTFE tubing that had a diameter of $\frac{1}{16}$". The fluid from manifold 6 is delivered to enclosure 34 via thermal member 46 through orifice 56 and returned through a fluid return (not shown) to manifold 6. In an embodiment, fluid communication of the fluid in flow member 8 is arranged in a countercurrent flow wherein fluid provided to thermal member 46 (through second fluid supply member 60) flows in a countercurrent direction with respect to the fluid moving in the fluid return. It should be appreciated that although the thermal member 46 is disposed below capillary tube 38 and mount 36 in the photograph shown in FIG. 16, thermal member 46 can be disposed in various locations with respect to mount 36 in enclosure 34. Additionally, analyte sampler 4 is configured to fully enclose mount 36 and capillary tube 38 by closing lid 124 on analyte sampler 4. Further, although not shown in FIG. 16, enclosure 34 can be disposed in a thermally insulating material.

In an embodiment, analyte sampler 4 is a hand piece, e.g., as shown in FIG. 11. In a particular embodiment, analyte sampler 4 is a module, e.g., as shown in FIG. 16. It is contemplated that the hand piece or module can be used as a stand-alone analyte sampler to receive the analyte.

According to an embodiment, analyte sampler 4 is connected to probe 12 that is configured to receive the analyte. In a certain embodiment, probe 12 is a standoff probe. Probe 12 samples a vapor space remotely and provides a margin of safety to a user or equipment. Probe 12 can sample vapor inside of an item such as a suitcase, shipboard cargo container, through soil or concrete, and the like. FIG. 17 shows a photograph of a probe 12 that includes probe 13 disposed at an end of probe 12 opposing probe adapter 19, body 17 to separate probe tip 13 from probe adapter 19, and a sampling orifice 15 disposed proximate to the probe tip 13 on a side of body 17. FIG. 18 shows an enlarged view of portion being indicated by the dashed rectangle in FIG. 17. FIG. 19 shows a longitudinal cross-section of probe 12 along line D1-D1 shown in FIG. 18, and FIG. 20 shows a transverse cross-section of probe 12 along line D2-D2 shown in FIG. 19. Probe 12 includes liner 25 disposed in inner tube 23 that is disposed in outer tube 21. Flow path 27 is circumscribed by an inner diameter of liner 25.

Materials used in construction of probe 12 are selected in recognition of the analyte. As such, the materials can be selected to be inert with respect to the activity with the analyte or other gas, liquid, or solid phase species or compositions to be sampled by probe 12. In an embodiment, probe 12 is rigid, robust, tolerates rough handling. According to an embodiment, probe 12 is flexible and can be bent at a selected angle, e.g., 0° to 325°. In an embodiment, probe 12 can be coiled.

Outer tube 21, Inner tube 23, and liner 25 independently can be made from a metal, plastic, glass, ceramic, and the like. In an embodiment, outer tube 21 and inner tube 23 independently are a metal. In a further embodiment, the metal is passivated, silanized, and the like to provide a selected low chemical activity to inner tube 23 or outer tube 21. In an embodiment, liner 25 is a fused silica tube, and inner tube 23 is a stainless steel tube. In the photograph shown in FIGS. 17 and 18, inner tube 23 has an outside diameter of 0.32 centimeters (cm) (0.125 inches (in)) and an inside diameter of 0.076 cm (0.030 in), and liner 25 was a fused silica tube disposed in inner tube 23 and had an inside diameter of 850 micrometers (μm) such that flow path 27 had a flow diameter of 850 μm.

Probe adapter 19 connects probe 12 with analyte sampler 4. In an embodiment, probe adapter 19 includes a crimp-type septum cap to connect to capillary tube 38 of an analyte sampler 4, e.g., shown in FIG. 11. In a certain embodiment, probe adapter 19 includes a compression fitting to connect to module analyte sampler shown in FIG. 16.

Analyte sampler 4 connects to manifold 6. With reference to FIG. 20, according to an embodiment, manifold 6 includes adapter 150 (e.g., a quick disconnect) that is configured to be connected to fluid source 16. In FIG. 20, arrows indicate direction of fluid communication. Fluid line 154 interconnects adapter 150 to valve 152 (e.g., a toggle valve) and valve 156 (e.g., 3-way valve). Valve 152 connects to vacuum member 64 at inlet 158 to supply the fluid from fluid source 16 and to exhaust fluid 16 at exhaust port 162 by which the a relative vacuum pressure (e.g., the negative pressure) is generated at vacuum port 160. The relative vacuum pressure generated by vacuum member 64 is produced, e.g., by the Bernoulli effect. In addition, valve 164 connects to vacuum port 160, and adapters 166, 170 are connected to valve 164. In this manner, valve 164 can be used to subject adapter 166 or adapter 170 to the negative pressure. Adapter 166 connects to vacuum line 10, and adapter 170 next to detector 22. Manifold 6 can include gauge 168 (e.g., a pressure gauge) to monitor pressure in fluid line 154. Accordingly, adapter 166 is configured to receive a fluid, analyte, or combination thereof from vacuum line 10 and to communicate the fluid vacuum member 64, which transmits the fluid to fluid dump 172 (e.g., a noise muffler, storage reservoir, and the like). Valve 164 can isolate adapter 166 from vacuum member 64, connect adapter 166 to vacuum member 64, or connect adapter 166 to adapter 170. Similarly, valve 164 can isolate or connect adapter 170 to vacuum member 64 or adapter 166.

Manifold 6 also includes first vortex tube 74 that connects to valve 156 at inlet 174 to receive fluid 16 from valve 156 and to communicate fluid 16 to fluid dump 184 via exhaust 176. In this manner, first vortex tube 74 produces a cold fluid at outlet 178 that is communicated to valve 180 via first fluid line 78 to be transmitted to fluid flow connector 182. Similarly, second vortex tube 76 connects to valve 156 at inlet 186 to receive fluid 16 from valve 156 and to communicate fluid 16 to fluid dump 184 via exhaust 188. In this manner, second vortex tube 76 produces a hot fluid at outlet 190 that is communicated to valve 180 via second fluid line 80 to be transmitted to fluid flow connector 182. As a result, valve 180 is configured to select the cold fluid or the hot fluid respectively produced by first vortex tube 74 or second vortex tube 76 for communication to fluid flow connector 182. Fluid flow connector 182 is configured to connect to flow member 8 to supply the cold fluid or hot fluid to second fluid supply member 60, which is ultimately connected to first fluid supply member 48 of thermal member 46 disposed in analyte sampler 4. Also, fluid flow connector 182 is configured to receive fluid from analyte sampler 4 via fluid return 62. Here, the fluid received by fluid flow connector 182 from the fluid return 62 is transmitted to fluid dump 190.

Figure 21:
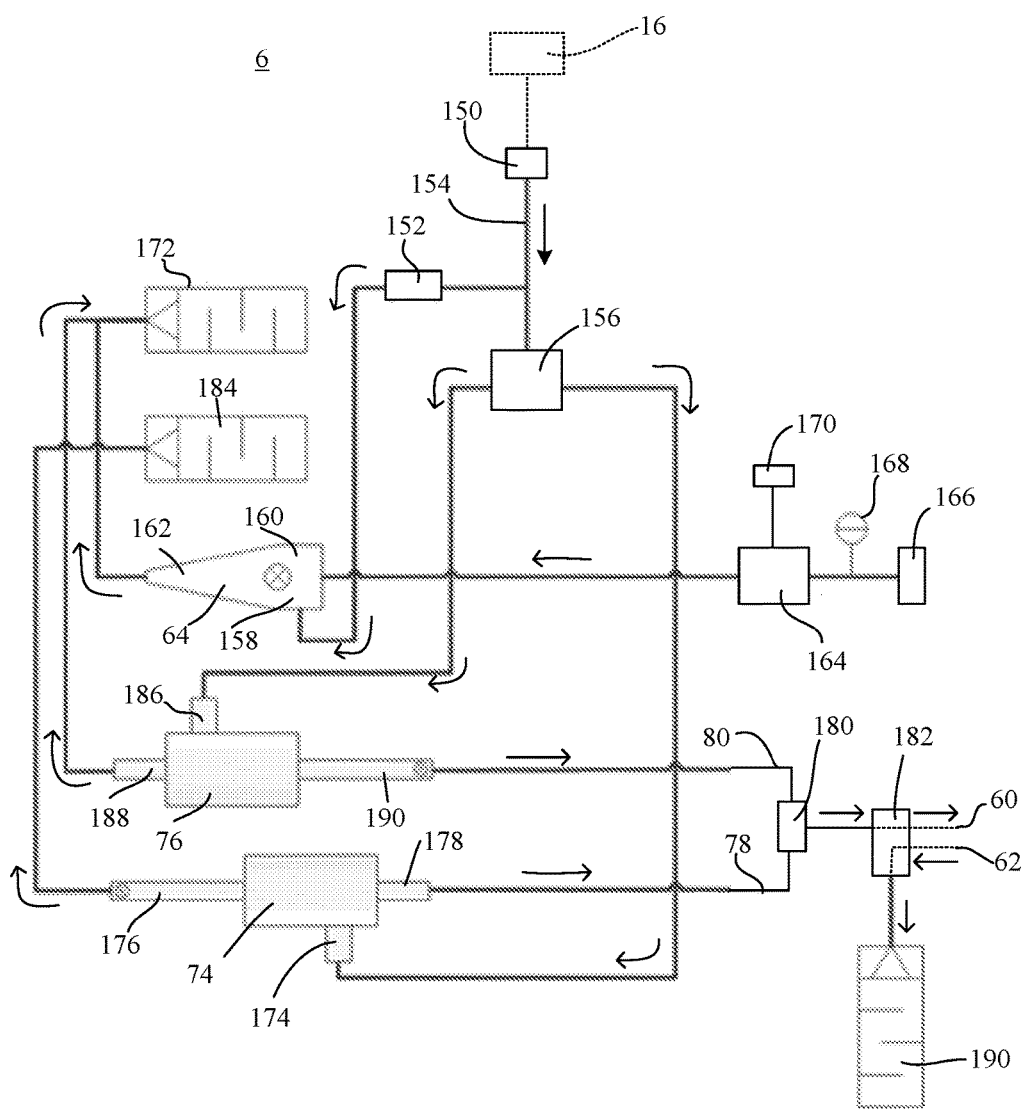
FIG. 21 shows a manifold.

According to an embodiment, manifold 6 includes temperature controller 70 that produces the cold fluid (e.g., by first vortex tube 74) or the hot fluid (e.g., by second vortex tube 76) from the fluid source. The cold fluid is communicated to capillary tube 38 to cryogenically absorb (i.e., cryoadsorption) the analyte on capillary tube 38, i.e., to cryogenically dispose and immobilize the analyte in capillary tube 38, which includes the PLOT column in a particular embodiment. The hot fluid is communicated to capillary tube 38 to desorb and mobilize the analyte in capillary tube 38. Manifold 6 also provides the negative pressure that is subjected to capillary tube 38 to communicate the analyte through capillary tube 38, i.e., for mass transfer of the analyte. In an embodiment, manifold 6 includes a quick disconnect (adapter 150) for connection to fluid source 16, first vortex tube 74 to generate the cold fluid, second vortex tube 76 to generate the hot fluid, vacuum member 64 (e.g., a pneumatic vacuum generator) and a controller to produce the negative pressure (e.g., suction), fluid dump (172, 184, 190, e.g., mufflers), and a plurality of insulated transfer lines (e.g., fluid line 154, first fluid line 78, second fluid line 80, and the like). In an embodiment, the elements of manifold 6 is shown in FIG. 21 (except fluid flow connector 182, second fluid supply member 60, and fluid return 62) are commercially available (but not in the arrangement shown in FIG. 21) and specified to perform the recited functions. Connections (e.g., fluid line 154) among elements of manifold 6 can be as short as possible in length (zero-length in some embodiments) and insulated to minimize heating and cooling losses. In an embodiment, the elements of manifold 6 are surrounded by a sound control sheet to control (e.g., reduce) noise from the elements of manifold 6. According to an embodiment, manifold 6 is disposed in a container. The container is rugged and reusable or can provide shock resistance to manifold 6. An exemplary container is an aluminum container that provides a sturdy, lightweight container such that manifold 6 disposed in the container is easily ported to a location.

In an embodiment, fluid source 16 is external to manifold 6. According to an embodiment, fluid source 16 is internal to manifold 6. Fluid source 16 provides the fluid at a selected pressure, flow rate, and the like. The pressure can be regulated from 0 pounds per square inch (psi) to 20,000 psi, specifically 0 psi to 10,000 psi, and more specifically zero psi to 1500 psi. The flow rate of the fluid from fluid source 16 can be from 90 standard cubic feet per minute (scfm) to 100 scfm. Fluid source 16 can be a tank that includes the fluid under compressed pressure, a fluid compressor, and the like. The fluid can be a gas, liquid, or accommodation thereof. Exemplary fluids include air, nitrogen, and the like. A temperature of the cold fluid can be from −40° C. to 0° C. A temperature of the hot fluid can be from 60° C. to 160° C.

Vacuum member 64, first vortex tube 74, second vortex tube 76, and flow member 8 each independently are configured to connect to fluid source 16, fluid dump (172, 184, 190), or a combination thereof. Exemplary fluid dumps 172, 184, 190 include a fluid exhaust, fluid reservoir, noise muffler, and the like.

With regard to flow member 8, flow member 8 is interposed between manifold 6 and analyte sampler 4 to communicate the fluid to analyte sampler 4 from manifold 6 and to return the fluid from analyte sampler 4 to manifold 6. In this manner, member 8 provides the hot fluid or the cold fluid to analyte sampler 4 (e.g., the hand piece, module, and the like). Accordingly, flow member 8 is configured to control the temperature of capillary tube 38, mount 36, and interior 35 of enclosure 34 of the analyte sampler 4. In an embodiment, flow member 8 provides both heating and cooling of capillary tube 38. According to an embodiment, the fluid is compressed air communicated by flow member 8 and eliminates a potential of a spark source such that a sampling system 2 or analyzer 20 is operable in explosive atmospheres, e.g., including Class I Division I Groups A and B locations of the National Electrical Code. In an embodiment, the directions of flows of fluid in flow member 8 (i.e., flow of the fluid in the fluid return 62 and second fluid supply member 60) counter propagate. Thus, flow member 8 provides countercurrent flow of the fluid for temperature control of capillary tube 38.

Figure 22:
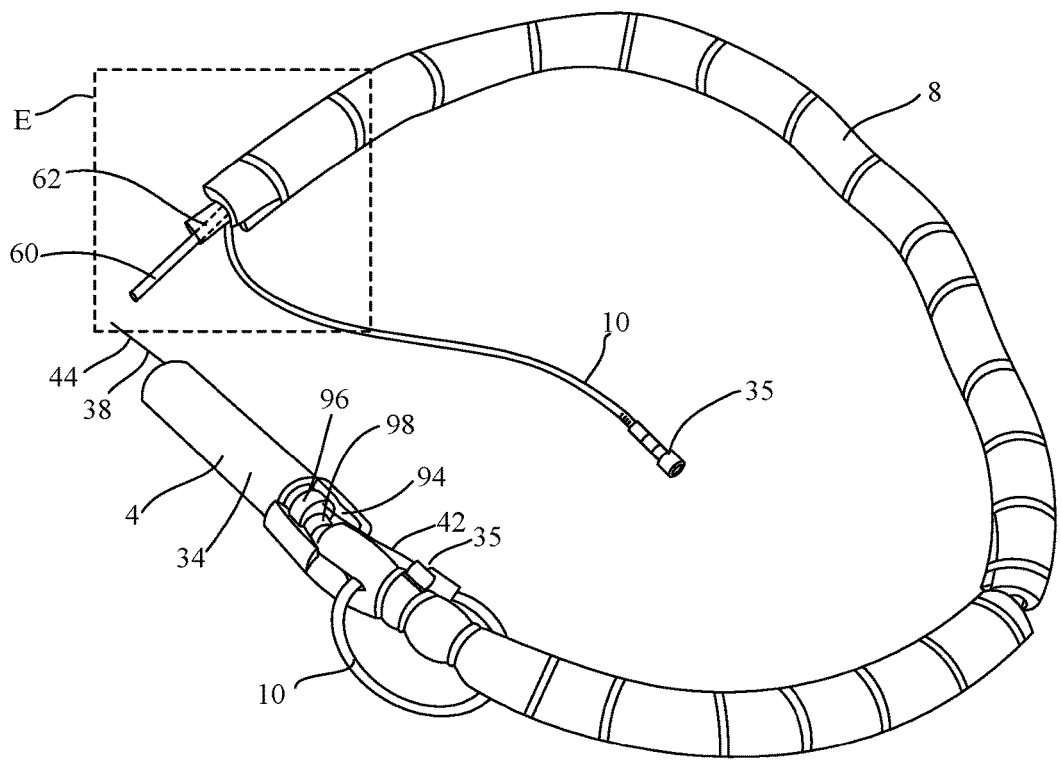
FIG. 22 shows a photograph of the analyte sampler connected to the flow member shown in FIG. 11.
Figure 23:
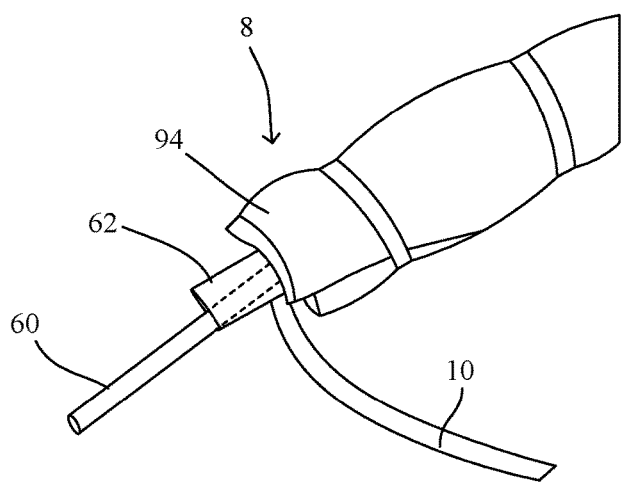
FIG. 23 shows a photograph of an enlarged view of portion A of the flow member shown in FIG. 22.
Figure 24:
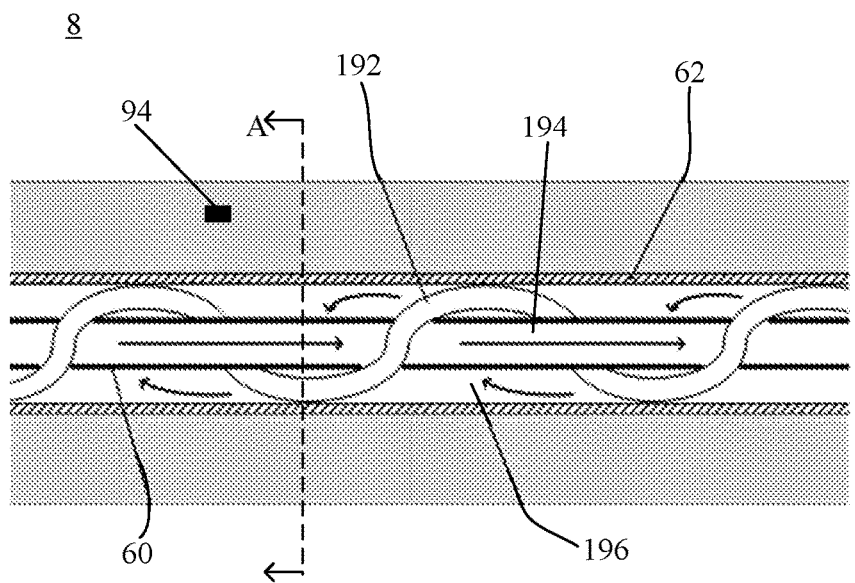
FIG. 24 shows a longitudinal cut away of a flow member.
Figure 25:
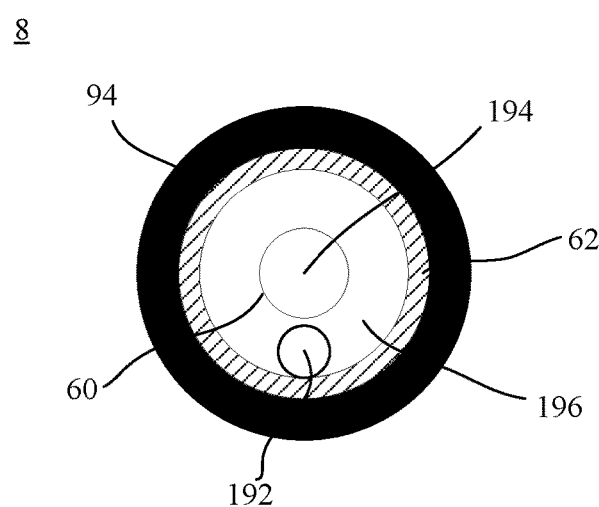
FIG. 25 shows a transverse cross-sectional along line A-A of the flow member shown in FIG. 24.

With reference to FIGS. 22, 23 (enlarged view of portion E shown in FIG. 22), 24, and 25, flow member 8 connects to analyte sampler 4 via vacuum line 10 and includes second fluid supply member 60 and fluid return 62. Installation 94 covers fluid supply member 60 and fluid return 62. As shown in the longitudinal cross-section of a flow member 8 of FIG. 24, second fluid supply member 60 is disposed in fluid return 62 and separated therefrom by spacer 192. Spacer 192 to be helical element surroundingly disposed about an outer surface of the second fluid supply member 60 such that fluid is communicated through second flow path 196 as a fluid return from analyte sampler 4 to manifold 6. Additionally, fluid from manifold 6 flows in second fluid supply member 64 toward analyte sampler 4 via first fluid path 194. Directions of fluid flow are indicated by arrows in FIG. 24 and indicate that the fluid counter propagates through flow member 8. A transverse cross-section of a flow member 8 along line A-A is shown in FIG. 25. Here, second fluid supply member 60 and fluid return 62 are coaxially arranged in an overlapping configuration with the second fluid supply member 60 disposed in the fluid return 62.

Second fluid supply member 60 can be a flexible material (e.g., semi flexible polyethylene and the like) and provides fluid delivery to analyte sampler 4 to communicate the cold fluid or the hot fluid. Second fluid supply member 60 can have an inner diameter effective to communicate the fluid, e.g., ¼-inch nominal outer diameter tube. Spacer 192 can be, e.g., a section of tubing with a nominal outer diameter (OD) of ⅜-inch and can be wound about second fluid supply member 60 to provide the countercurrent return the fluid with second flow path 196 that is free of obstruction or choking. Spacer 192 can also minimize contact of second fluid supply member 60 with a surface of fluid return 62. Fluid return 62 can be tubing, e.g., with an outer diameter of ¾-inch and in inner diameter of ½-inch. In this manner, the fluid return 62 is configured to c second fluid supply member 60 and spacer 192 to provide internal disposition of the countercurrent flow of the fluid. Installation 94 provides thermal insulation of fluid return 62, second fluid supply member 60, and spacer 192. Flow member 8 can have a length effective to communicate the fluid from manifold 6 to analyte sampler 4 so that a temperature of the fluid is not changed beyond a temperature selected to cool or heat capillary tube 38. According to an embodiment, flow member 8 can have a length from 5 centimeters (cm) to 3 meters (m) or greater, specifically 10 cm to 2 m.

Figure 26:
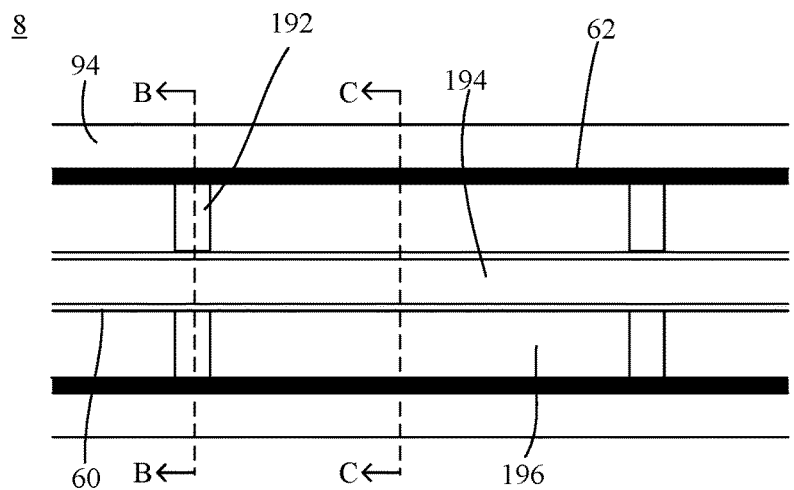
FIG. 26 shows a longitudinal cross-section of a flow member.
Figure 27:
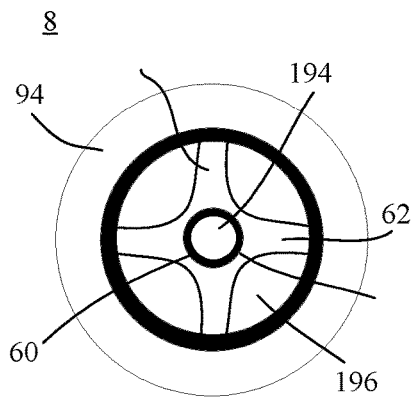
FIG. 27 shows a transverse cross-section along line B-B of the flow member shown in FIG. 26.
Figure 28:
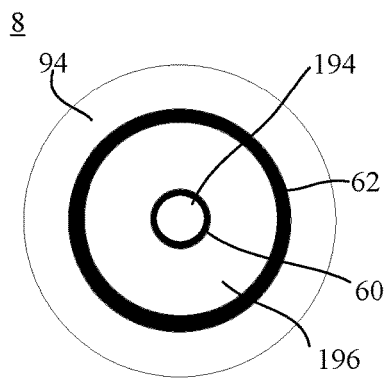
FIG. 28 shows a transverse cross-section along line C-C of the flow member shown in FIG. 26.
Figure 29:
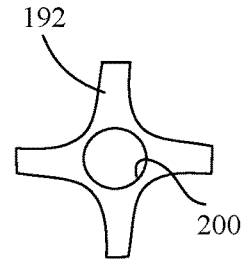
FIG. 29 shows a transverse cross-section along line B-B of a spacer shown in FIG. 26.

An embodiment of flow member 8 is shown in FIGS. 26 (longitudinal cross-section), 27 (transverse cross-section of flow member 8 along line B-B shown in FIG. 26), 28 (transverse cross-section of the flow member 8 along line C-C shown in FIG. 26), and 29 (transverse cross-section of spacer 192 along line B-B shown in FIG. 26). Here, installation 94 is disposed over fluid return 62 in which second fluid supply member 60 is disposed. A plurality of spacers 194 separates an outer wall of second fluid supply member 60 from an inner wall of fluid return 62. Spacer 194 includes orifice 200 through which second fluid supply member 60 is disposed. Second fluid supply member 60 provides first flow path 194 through which the fluid is communicated from manifold 6 to analyte sampler 4. Spacer 192 is a shape, e.g., as shown in FIG. 29, effective to provide second flow path 196 in fluid return 62 so that the fluid is communicated from analyte sampler 4 to manifold 6 without having constrained flow that interrupts fluid communication therethrough. Here, second fluid supply member 60 and fluid return 62 are coaxially arranged in an overlapping configuration with the second fluid supply member 60 disposed in the fluid return 62.

Figure 30:
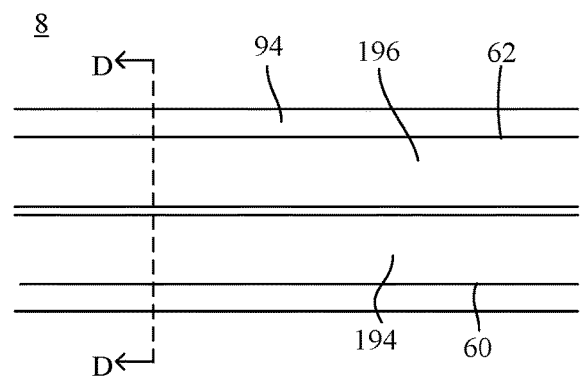
FIG. 30 shows a longitudinal cross-section of a flow member.
Figure 31:
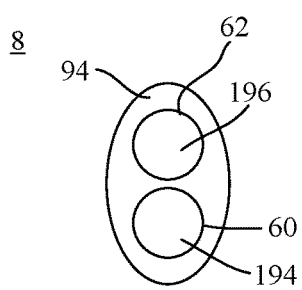
FIG. 31 shows a transverse cross-section along line D-D of the flow member shown in FIG. 30.

According to an embodiment of flow member 8 as shown in FIGS. 30 (longitudinal cross-section) and 31 (transverse cross-section of flow member 8 along line D-D shown in FIG. 30)31, flow member 8 includes second fluid supply member 60 and fluid return 62 respectively having first flow path 194 and second flow path 196. Here, second fluid supply member 60 and fluid return 62 are arranged in a parallel configuration without overlap and are therefore not coaxial.

Figure 32:
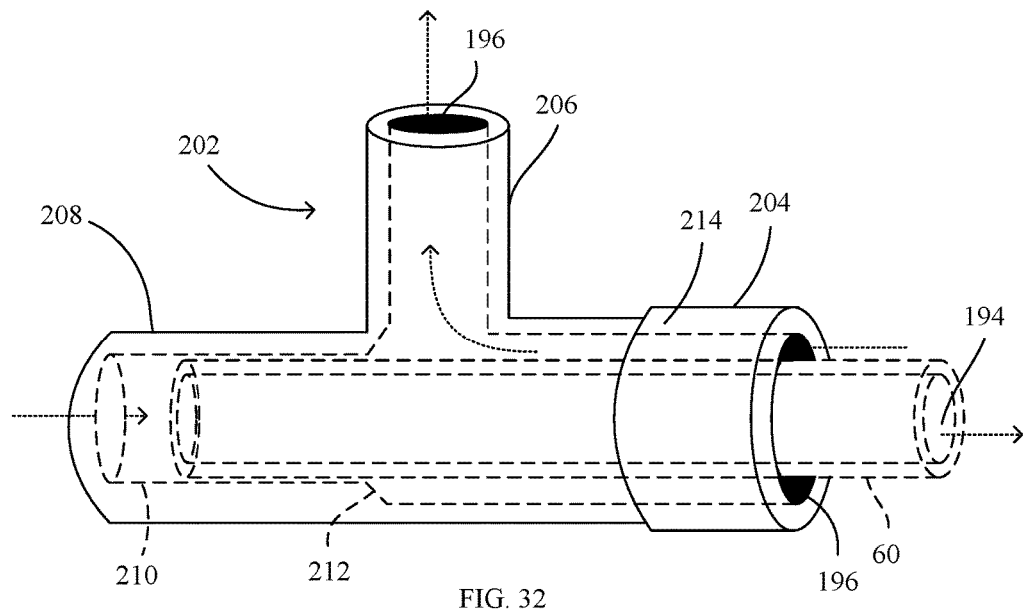
FIG. 32 shows a perspective view of a manifold adapter.
Figure 33:
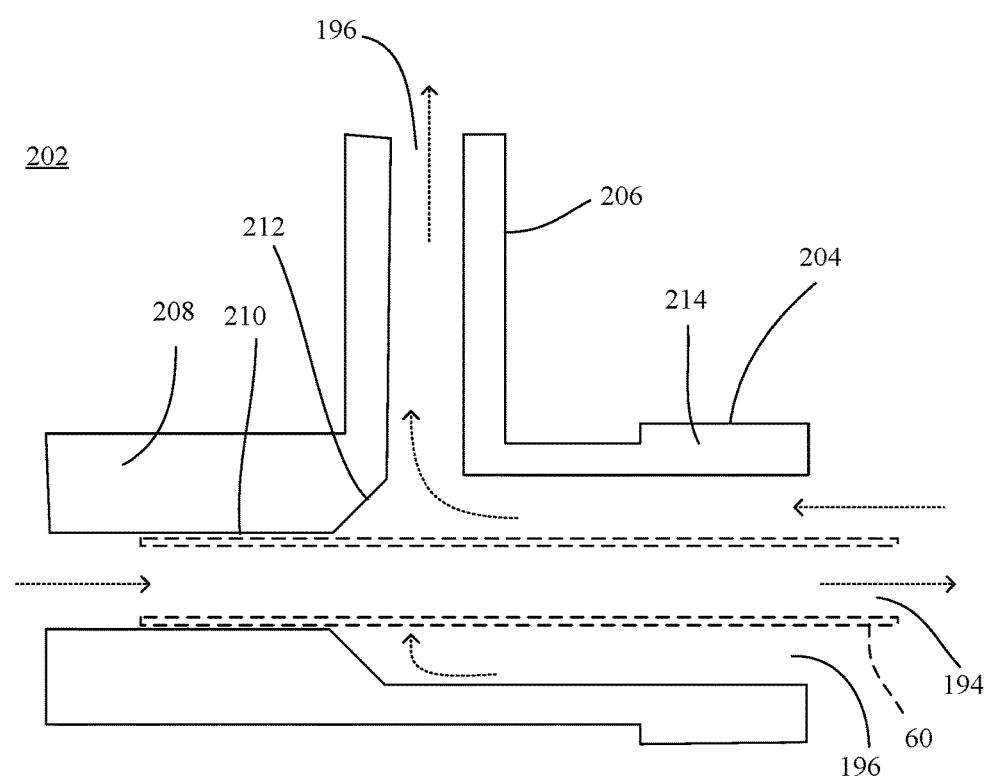
FIG. 33 shows a longitudinal cross-section of the manifold adapter shown in FIG. 32.

According to an embodiment, flow member 8 is in fluid communication with temperature controller 70, particularly the first vortex tube 74 or second vortex tube 76, for receipt of the cold fluid or the hot fluid through fluid flow connector 182. The fluid flow connector can be a compression fitting or manifold adapter 202 shown in FIG. 32 (perspective view) or 33 (transverse cross-sectional view). A plurality of manifold adapters 202, valves 180, or a combination thereof can be provided to select or communicate the cold fluid or the hot fluid.

Manifold adapter 202 includes mating surface 204 to attach to flow member 8 (e.g., a compression fitting such as a quick disconnect) and to interface with second fluid supply member 60 (e.g., through a press fit of second fluid supply member 60 in seal surface 210 disposed at an end of manifold adapter 202 proximate to guide 212 Guide 212 can be, e.g., a chamfer to guide second fluid supply member 60 for seating it into sealing disposal into manifold adapter 202. In this arrangement, first flow path 194 is provided through manifold adapter 202 and second fluid supply member 60. Second flow path 196 is provided through manifold adapter 202 and return port 206 and external to second fluid supply member 60, when present. Supply port 208 is provided to connect manifold adapter 202 to manifold 6, e.g., valve 180, first fluid line 78, second fluid line 80, and the like. Return port 206 is configured to communicate fluid from flow member 8 along second flow path 196, e.g., to fluid dump 190 disposed in manifold 6. Supply port 208, return port 206, or connector 214 can be arranged at any angle with respect to each other, where the angle is effective so that manifold adapter 202 communicates the fluid between manifold 6 and flow member 8.

Manifold adapter 202 is configured to provide flow of the fluid at a selected temperature that is jacketed or insulated by a spent or return fluid. In an embodiment, first vortex tube 74 is configured to provide the cold fluid to cool capillary tube 38 such that the cold fluid is communicated in second fluid supply member 60. The fluid returned from analyte sampler 4, instead of being discharged out of the hand piece or module, is returned (routed around second fluid supply member 60) in fluid return 62 to provide insulation and to minimize a temperature rise due to an environment external to flow member 8.

When fluid is returned to manifold 6 through manifold adapter 202, fluid is communicated to fluid dump 190 and discharged, e.g., to a storage reservoir or the atmosphere. Sound control sheets can be present in or on manifold 6 to minimize noise created from discharge of fluid from fluid dumps 190, 172, 184. In an embodiment, to communicate the hot fluid to capillary tube 38, e.g., to desorb the analyte from the PLOT capillary, the same flow member 8 is used, but flow member 8 is connected to a different manifold adapter 202 connected to second vortex tube 76 rather than first vortex tube 74.

Without wishing to be bound by theory, it is believed that the sampling system and analyzer have numerous beneficial advantages and properties. The sampling system is a field portable vapor collection device configure to sample vapors of high and medium volatility solutes, including polar solutes at a location that is remote from a laboratory. The sampling system can be used with thermal desorption or solvent elution of the acquired analyte in analyte sampler 4 with and without a thermal assist. The sampling system is configured for use with elution of a reagent instead of a solvent, such as a ninhydrin solution, to perform presumptive testing on the analyte. The sampling system is configure to be self-cleaning such that after elution of the analyte from capillary tube 38 heating prepares the sampling system for a next sample collection of an analyte.

Further, the sampling system is configure for use a plurality of times (e.g., consecutive uses) in the field without analyzing the collected analyte between serial collections. The sampling system is configured to operate pneumatically without application of electrical power. According to an embodiment, the sampling system is configured to operate on a fluid source of compressed air available in a field location, e.g., from a fire, crime scene, or law enforcement vehicle, and the like. In some embodiments, the sampling system is configured to operate entirely with compressed air such that the sampling system does not include a spark source, e.g., for operation in a presence of a flammable vapor or dust (e.g., as provided for in Class I, Division I, Groups A and B of the U.S. National Electrical Code).

Probes and elements described herein are contemplated for use with the sampling system for sampling in soil, beneath articles (e.g., a concrete slab), inside a shipboard cargo container, suitcase, and the like. Moreover, the sampling system is robust and rugged, and, in some embodiments does not include a moving part. Capillary tube 38 has a long lifetime since it disposed in a protective mount 36. Furthermore, a plurality of capillary tubes disposed in a mount can be disposed in analyte sampler 4 (e.g., a hand piece or module) and can be used independently, serially, in parallel, simultaneously, or asynchronously.

In an embodiment, a process for sampling an analyte includes subjecting a capillary tube disposed in an analyte sampler to a negative pressure. The analyte sampler includes an enclosure; a mount disposed in the enclosure; the capillary tube disposed in the mount and configured to receive the analyte; and a thermal member disposed in the enclosure and configured to pneumatically control a temperature of the capillary tube, the thermal member comprising a first fluid supply member to provide a fluid to an interior of the enclosure. The process also includes controlling the temperature of the capillary tube, wherein the temperature is effective to immobilize the analyte in the capillary tube; providing an analyte to a first end of the capillary tube; and immobilizing the analyte in the capillary tube to sample the analyte. The process further includes heating the capillary tube to mobilize the analyte in the capillary tube; communicating the analyte from the capillary tube to a detector; and detecting the analyte.

The articles and processes herein are illustrated further by the following Examples, which are non-limiting.

EXAMPLES

Example 1. Analyte Sampling

Figure 34A:
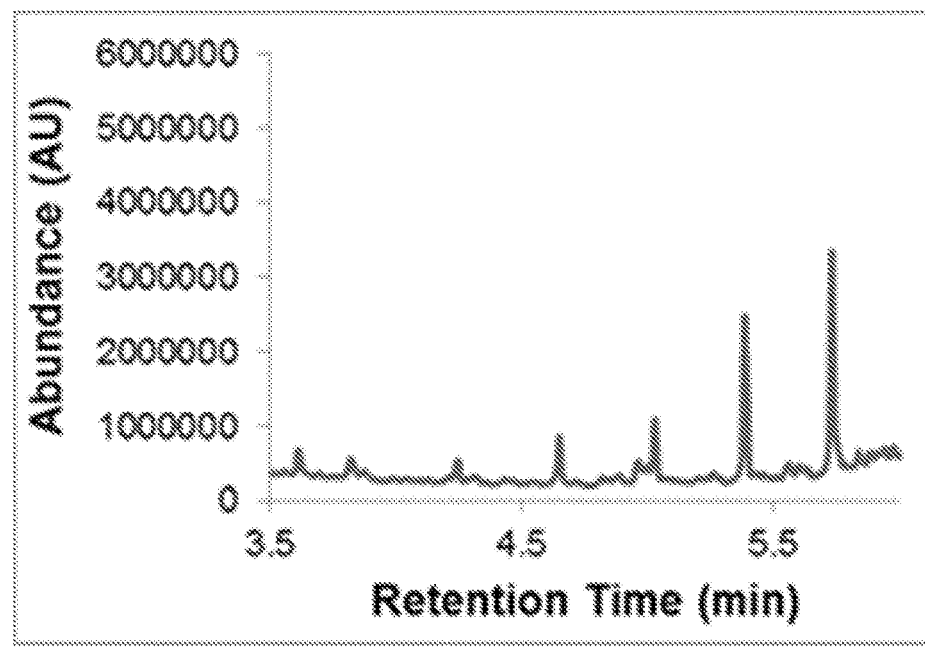
FIGS. 34A, 34B, 34C, and 34D show graphs of abundance versus retention time according to Example 1.
Figure 34B:
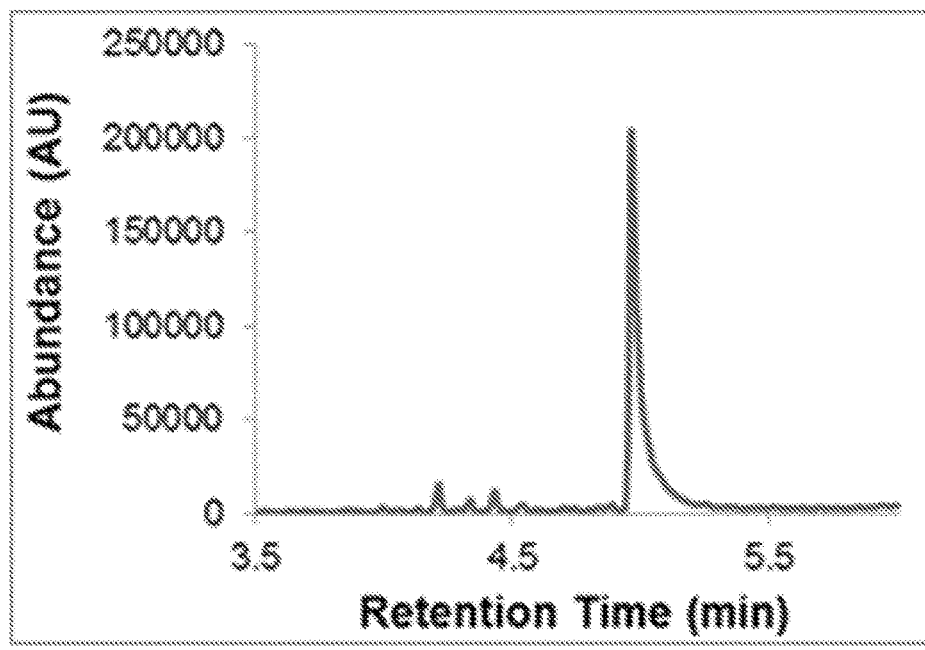
Figure 34C:
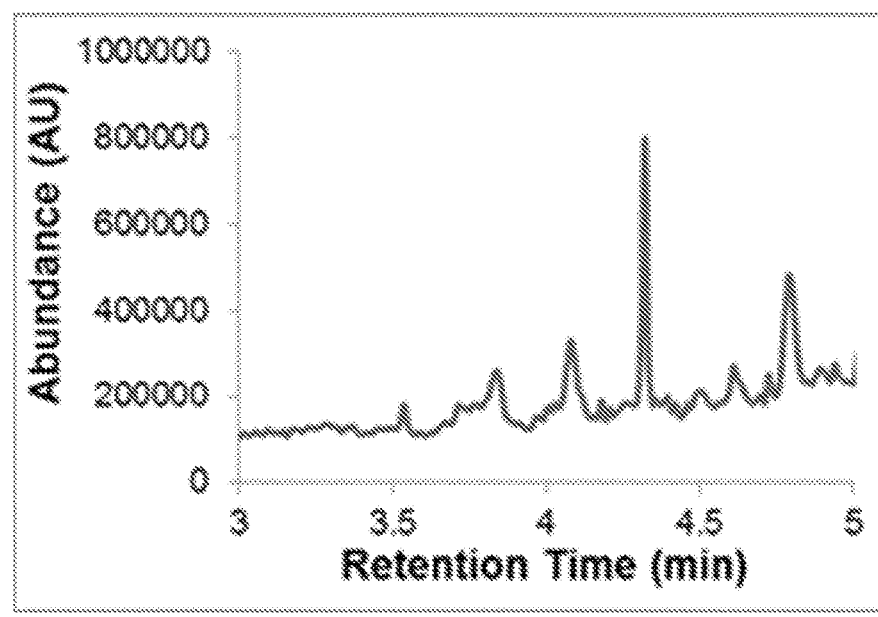
Figure 34D:
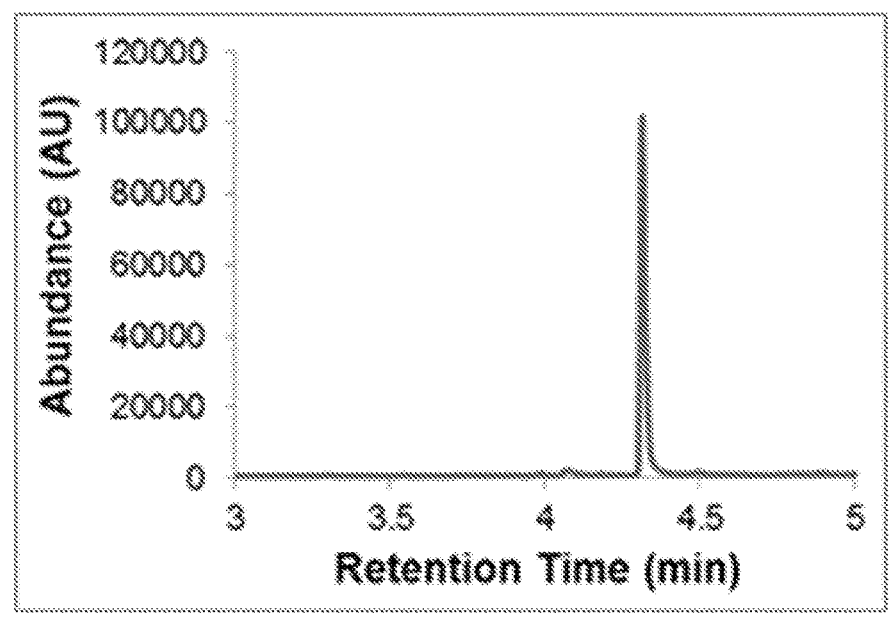

A field portable sampling system included a capillary tube having a PLOT capillary. The capillary tube was used to separately acquire two different analytes (coumarin and 1,3,5-trinitrotoluene) from various samples. In a first sample, coumarin was disposed on glass beads. In a second sample, 1,3,5-trinitrotoluene was disposed on glass beads. These two analytes were disposed as the first or second sample in vented scintillation vials. Vapor from the first sample and the second was collected for time periods of 10 and 30 minutes for both samples using a hand piece configuration of the analyte sample and a module configuration of the analyte sampler. After acquisition of the analytes, the flow member was removed from the cold air manifold adapter and connected to the hot air manifold adapter (to heat the respective PLOT capillary from 60° C. to 80° C.). The PLOT capillary was then solvent eluted with 1 mL of acetone and the resulting solution was collected in an automatic sampler vial. The collected solutions were analyzed by gas chromatography-mass spectrometry (GC-MS) in both scan and selected ion monitoring modes. Analytes (coumarin and 1,3,5-trinitrotoluene) were identified in the chromatograms. Representative chromatograms presented in scan and SIM modes of gas chromatography mass spectrometry are shown in FIG. 34, with chromatograms showing the analysis of coumarin (FIG. 34A: scan mode; FIG. 34B: SIM mode) and TNT (FIG. 34C: scan mode; FIG. 34D: SIM mode) from the recovered solution after collection from vapor headspace by use of the portable PLOT-cryoadsorption method. Chromatographic conditions were as described in the text. The abundance axis is in arbitrary units.

Example 2. Aviation Fuel Sampling

Figure 35A:
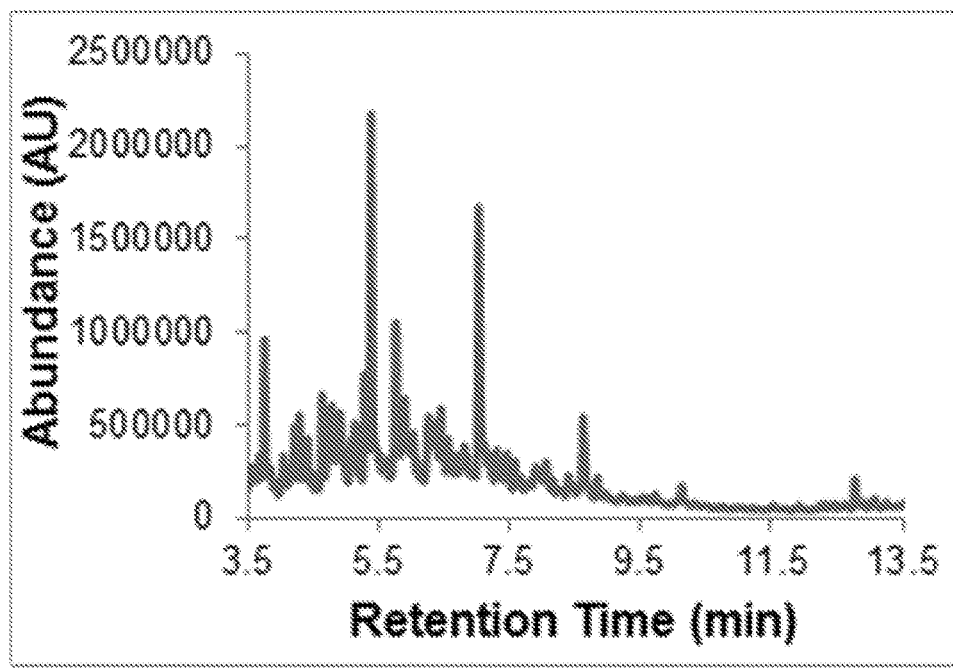
FIGS. 35A and 35B show graphs of abundance versus retention time according to Example 2.
Figure 35B:
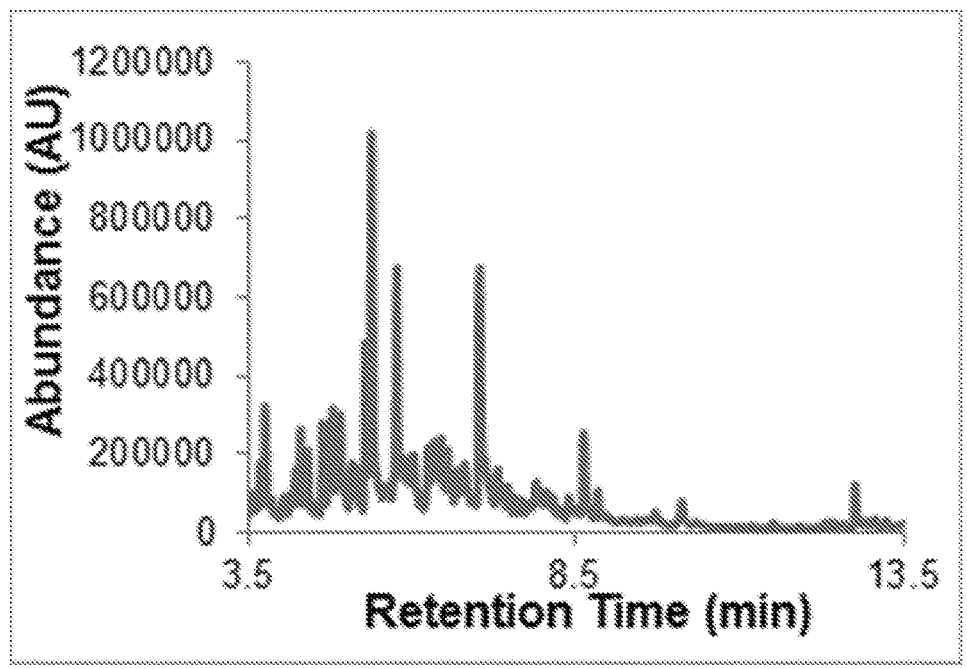

A sample of military aviation turbine kerosene JP-5 was prepared by disposing a drop of the JP-5 in a paint can (118 mL, 4 oz.). The sample was collected for 30 seconds in a similar fashion as described in Example 1. Gas chromatograms showed typical analyses for vapor samples produced at ambient temperature and are shown in FIGS. 35A (scan mode) and 35 B (results from SIM).

Example 3. Naphthalene Sampling

Figure 36A:
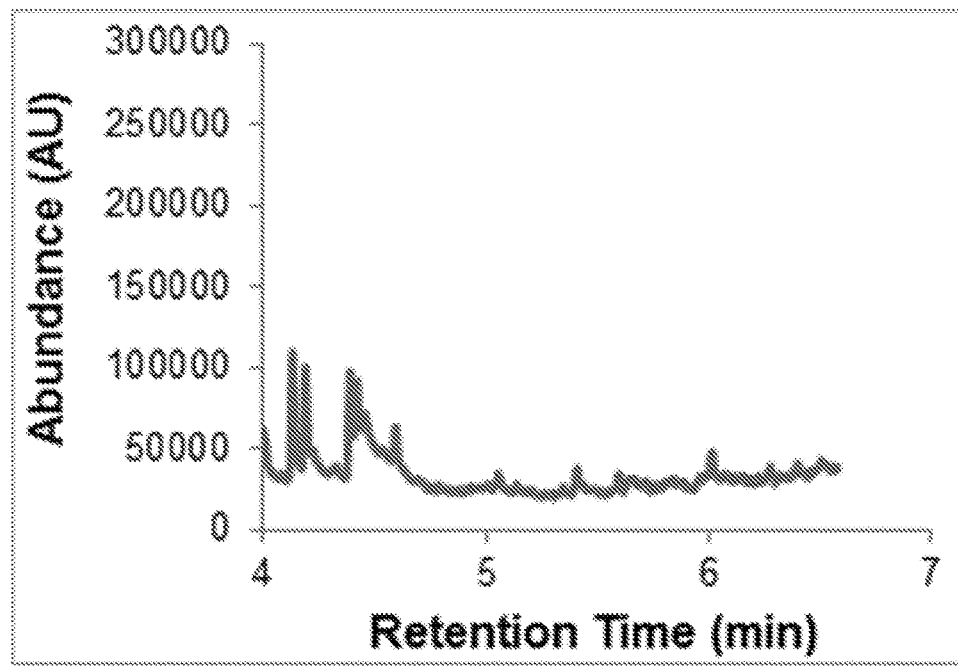
FIGS. 36A and 36B show graphs of abundance versus retention time according to Example 3.
Figure 36B:
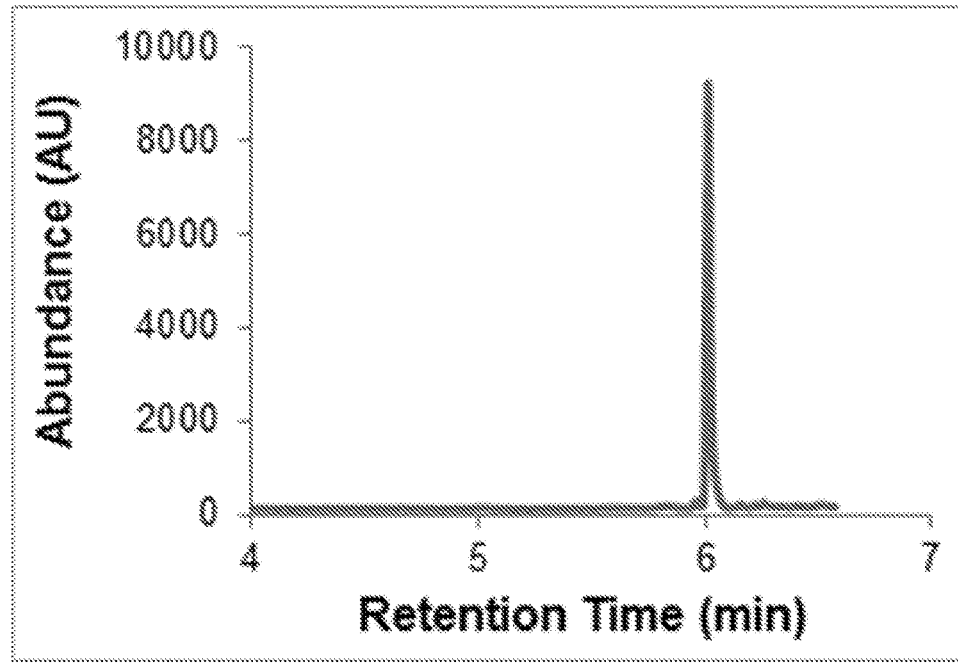

A sample of naphthalene was prepared by disposing approximately 50 mg of naphthalene in a valise and equilibrating the internal atmosphere of the valise at ambient temperature. Vapor from inside the valise was sampled for 3 seconds under the conditions of Example 1. Gas chromatography mass spectrometry results are shown in FIG. 36A (scan mode) and FIG. 36B (results from SIM). Analyses indicated presence of naphthalene.

While one or more embodiments have been shown and described, modifications and substitutions may be made thereto without departing from the spirit and scope of the invention. Accordingly, it is to be understood that the present invention has been described by way of illustrations and not limitation. Embodiments herein can be used independently or can be combined.

All ranges disclosed herein are inclusive of the endpoints, and the endpoints are independently combinable with each other. The ranges are continuous and thus contain every value and subset thereof in the range. Unless otherwise stated or contextually inapplicable, all percentages, when expressing a quantity, are weight percentages. The suffix "(s)" as used herein is intended to include both the singular and the plural of the term that it modifies, thereby including at least one of that term (e.g., the colorant(s) includes at least one colorants). "Optional" or "optionally" means that the subsequently described event or circumstance can or cannot occur, and that the description includes instances where the event occurs and instances where it does not. As used herein, "combination" is inclusive of blends, mixtures, alloys, reaction products, and the like.

As used herein, "a combination thereof" refers to a combination comprising at least one of the named constituents, components, compounds, or elements, optionally together with one or more of the same class of constituents, components, compounds, or elements.

All references are incorporated herein by reference.

The use of the terms "a" and "an" and "the" and similar referents in the context of describing the invention (especially in the context of the following claims) are to be construed to cover both the singular and the plural, unless otherwise indicated herein or clearly contradicted by context. "Or" means "and/or." It should further be noted that the terms "first," "second," "primary," "secondary," and the like herein do not denote any order, quantity, or importance, but rather are used to distinguish one element from another. The modifier "about" used in connection with a quantity is inclusive of the stated value and has the meaning dictated by the context (e.g., it includes the degree of error associated with measurement of the particular quantity). The conjunction "or" is used to link objects of a list or alternatives and is not disjunctive; rather the elements can be used separately or can be combined together under appropriate circumstances.

What is claimed is:

1. A sampling system comprising:
an analyte sampler comprising:
an enclosure;
a mount disposed in the enclosure;
a capillary tube disposed in the mount and configured to receive an analyte; and
a thermal member disposed in the enclosure and configured to pneumatically control a temperature of the capillary tube, the thermal member comprising a first fluid supply member to provide a fluid to an interior of the enclosure;
a manifold in fluid communication with the analyte sampler;
a flow member to interconnect the manifold and the analyte sampler, the flow member comprising:
a second fluid supply member to communicate the fluid from the manifold to the first fluid supply member; and
a fluid return to communicate the fluid from the enclosure to the manifold;
a thermal insulation surroundingly disposed on the second fluid supply member or the fluid return; and
a spacer interposed between the second fluid supply member and the thermal insulation,
wherein flow member is configured such that a direction of flow of the fluid in the second fluid supply member is counter to a direction of flow of the fluid in the fluid return.

2. The sampling system of claim 1, wherein the second fluid supply member and the fluid return are coaxially disposed in the flow member.

3. The sampling system of claim 1, wherein the second fluid supply member and the fluid return are adjacently disposed in the flow member.

4. The sampling system of claim 1, wherein the thermal member is configured to pneumatically control the temperature of the capillary tube from −40° C. to 160° C.

5. The sampling system of claim 1, wherein the sampling system is configured to receive the analyte in the capillary tube in an amount effective to be detected by an analytical instrument, and an acquisition time to receive the analyte in the capillary tube in the amount effective is less than 5 seconds.

6. The sampling system of claim 1, wherein the enclosure is configured to receive the fluid from the second fluid supply member and to recycle the fluid to the fluid return.

7. The sampling system of claim 1, wherein the capillary tube comprises a porous layer open tubular column.

8. The sampling system of claim 1, wherein the enclosure is a hand piece or sampling module.

9. The sampling system of claim 8, wherein the vacuum member, the first vortex tube, the second vortex tube, and the flow member independently are configured to connect to a fluid source, a fluid dump, or a combination comprising at least one of the foregoing.

10. The sampling system of claim 1, further comprising:
a vacuum member to generate a negative pressure; and
a vacuum line to connect the vacuum member to a second end of the capillary tube and to subject an interior of the capillary tube to the negative pressure.

11. The sampling system of claim 10, wherein the negative pressure is from −20 Pa to −25 kPa, relative to a standard atmosphere.

12. The sampling system of claim 10, further comprising a temperature controller to selectively control a temperature of the thermal member.

13. The sampling system of claim 10, further comprising a probe connected to a first end of the capillary tube.

14. The sampling system of claim 13, wherein the temperature controller comprises:
a first vortex tube to produce a cold fluid; and
a second vortex tube to produce a hot fluid,
wherein the fluid provided to the interior of the enclosure comprises the cold fluid or the hot fluid.

15. The sampling system of claim 14, wherein the manifold comprises:
the vacuum member;
the first vortex tube; and
the second vortex tube.

16. The sampling system of claim 13, wherein the probe comprises:
a body;
a probe tip disposed at an end of the body; and
a sampling orifice disposed proximate to the probe tip.

* * * * *